United States Patent
Ruane et al.

(10) Patent No.: US 11,701,449 B2
(45) Date of Patent: Jul. 18, 2023

(54) HYDROGEL COMPOSITION FOR MUCOSAL LIFTING PROCEDURES WITHIN LUMENAL ANATOMICAL STRUCTURES

(71) Applicant: QMARK MEDICAL INC., Saint Paul, MN (US)

(72) Inventors: Patrick H. Ruane, Dublin, CA (US); Sameer Sharma, New York, NY (US)

(73) Assignee: QMARK MEDICAL INC., St. Paul, MN (US)

( * ) Notice: Subject to any disclaimer, the term of this patent is extended or adjusted under 35 U.S.C. 154(b) by 0 days.

(21) Appl. No.: 18/056,109

(22) Filed: Nov. 16, 2022

(65) Prior Publication Data

US 2023/0072543 A1    Mar. 9, 2023

Related U.S. Application Data

(63) Continuation of application No. 17/415,775, filed as application No. PCT/US2019/067966 on Dec. 20, 2019.

(60) Provisional application No. 62/784,213, filed on Dec. 21, 2018.

(51) Int. Cl.
| | |
|---|---|
| *A61L 27/20* | (2006.01) |
| *A61K 31/738* | (2006.01) |
| *A61L 27/16* | (2006.01) |
| *A61L 27/18* | (2006.01) |
| *A61L 27/52* | (2006.01) |
| *A61L 27/54* | (2006.01) |

(52) U.S. Cl.
CPC ............ *A61L 27/20* (2013.01); *A61K 31/738* (2013.01); *A61L 27/16* (2013.01); *A61L 27/18* (2013.01); *A61L 27/52* (2013.01); *A61L 27/54* (2013.01)

(58) Field of Classification Search
CPC ................................ A61K 27/20; A61K 27/52
See application file for complete search history.

(56) References Cited

U.S. PATENT DOCUMENTS

| | | | |
|---|---|---|---|
| 6,562,362 B1 * | 5/2003 | Bae | A61L 24/06 424/424 |
| 7,700,086 B2 | 4/2010 | Schwarz | |
| 7,909,809 B2 | 3/2011 | Scopton et al. | |
| 8,864,738 B2 | 10/2014 | Scopton et al. | |
| 9,226,996 B2 | 1/2016 | Moro et al. | |
| 2001/0053897 A1 | 12/2001 | Frate et al. | |
| 2004/0266983 A1 | 12/2004 | Reeve et al. | |
| 2006/0280797 A1 | 12/2006 | Shoichet et al. | |
| 2011/0052490 A1 | 3/2011 | Vogel | |

(Continued)

FOREIGN PATENT DOCUMENTS

| | | |
|---|---|---|
| CN | 101932287 B | 12/2016 |
| WO | WO03/087019 A1 | 10/2003 |

OTHER PUBLICATIONS

Boolai et al.; Thermosensitive poloxamer 407/poly(acrylic acid) hydrogels with potential application as injectable drug delivery system; AAPS PharmSciTech; 19(5); pp. 2103-2117; Jul. 2018.

(Continued)

*Primary Examiner* — Carlos A Azpuru
(74) *Attorney, Agent, or Firm* — Shay Glenn LLP

(57) ABSTRACT

An injectable medical composition includes an acrylate and a solvent. The composition has a first viscosity at temperatures below body temperature and a second viscosity at body temperature. The first viscosity is lower than the second viscosity.

9 Claims, 12 Drawing Sheets

(56) References Cited

U.S. PATENT DOCUMENTS

2011/0172768 A1   7/2011  Cragg et al.
2015/0313838 A1  11/2015  Lichter et al.
2022/0062498 A1   3/2022  Ruane et al.

OTHER PUBLICATIONS

Dayyeh et al.; Endoscopic submucosal dissection; Gastrointestinal Endoscopy; 81(6); pp. 1311-1325 ; Jun. 2015.
Gostout; Ode to the submucosal fluid cushion: Endoscopy; 36(7); pp. 638-639; 3 pages (Abstract Only); Jul. 2004.
Lubrizol; Carbopol edt 2020 nf polymer (Product Specification): 1 page; retrieved from the internet (https://www.lubrizol.com/-/media/Lubrizol/Health/Literature/SPEC_Carbopol_ETD_2020_NF.pdf) on Jul. 14, 2021.
U.S. Food and Drug Administration; Dissolvable gel for preventing ureteral stone migration (Premarket Notification); 5 pages; retrieved from the internet (https://www.accessdata.fda.gov/scripts/cdrh/cfdocs/cfpmn/pmn.cfm?ID=K090430) on Jul. 14, 2021.

\* cited by examiner

Injectate

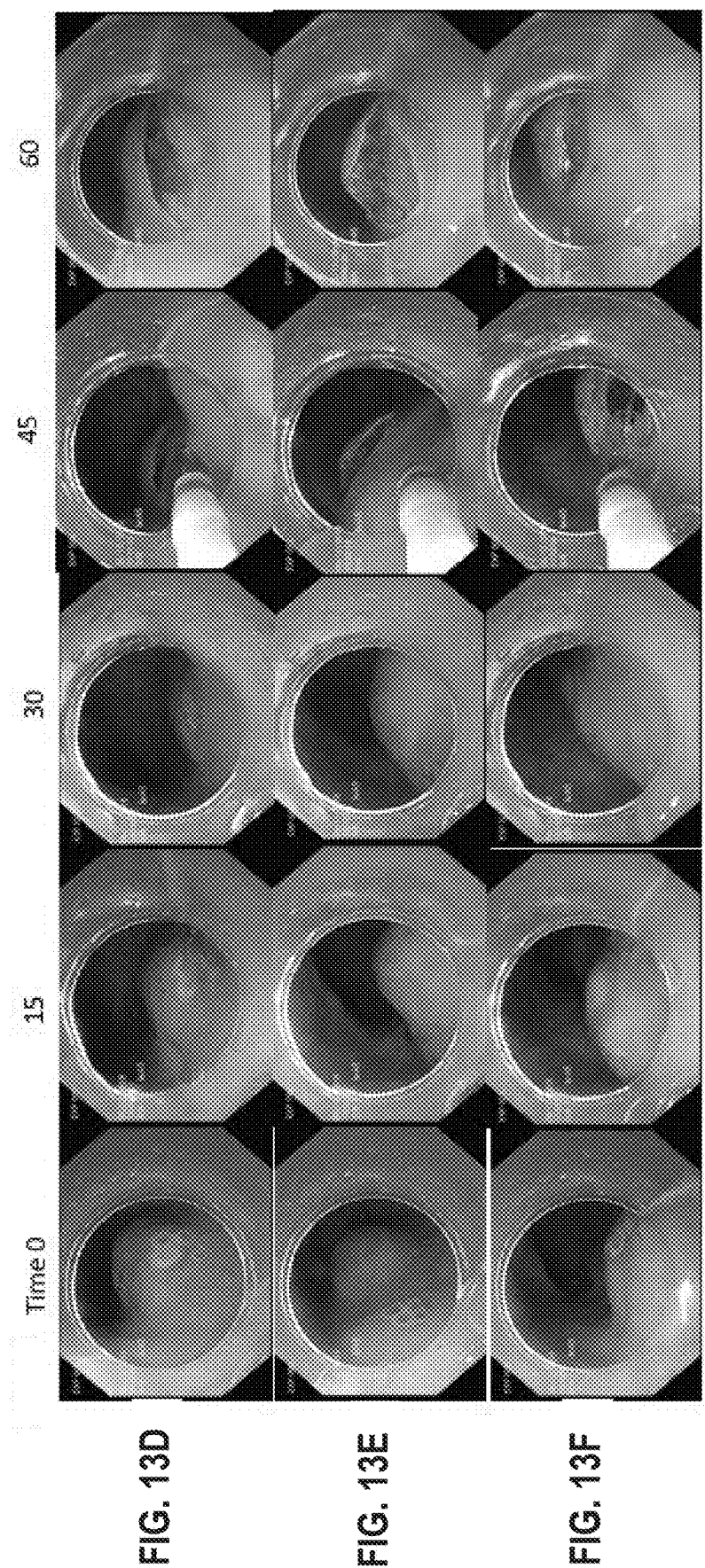

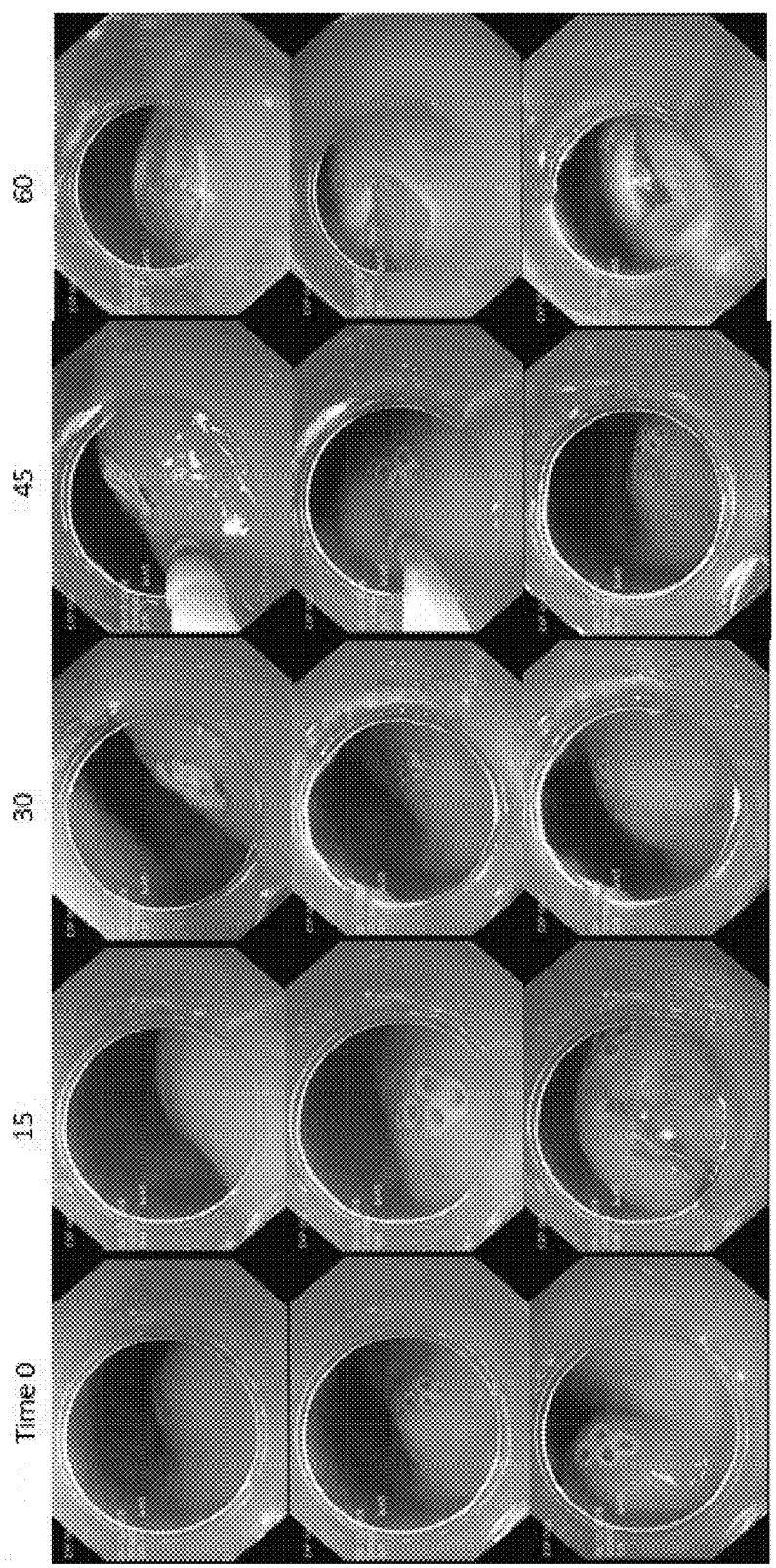

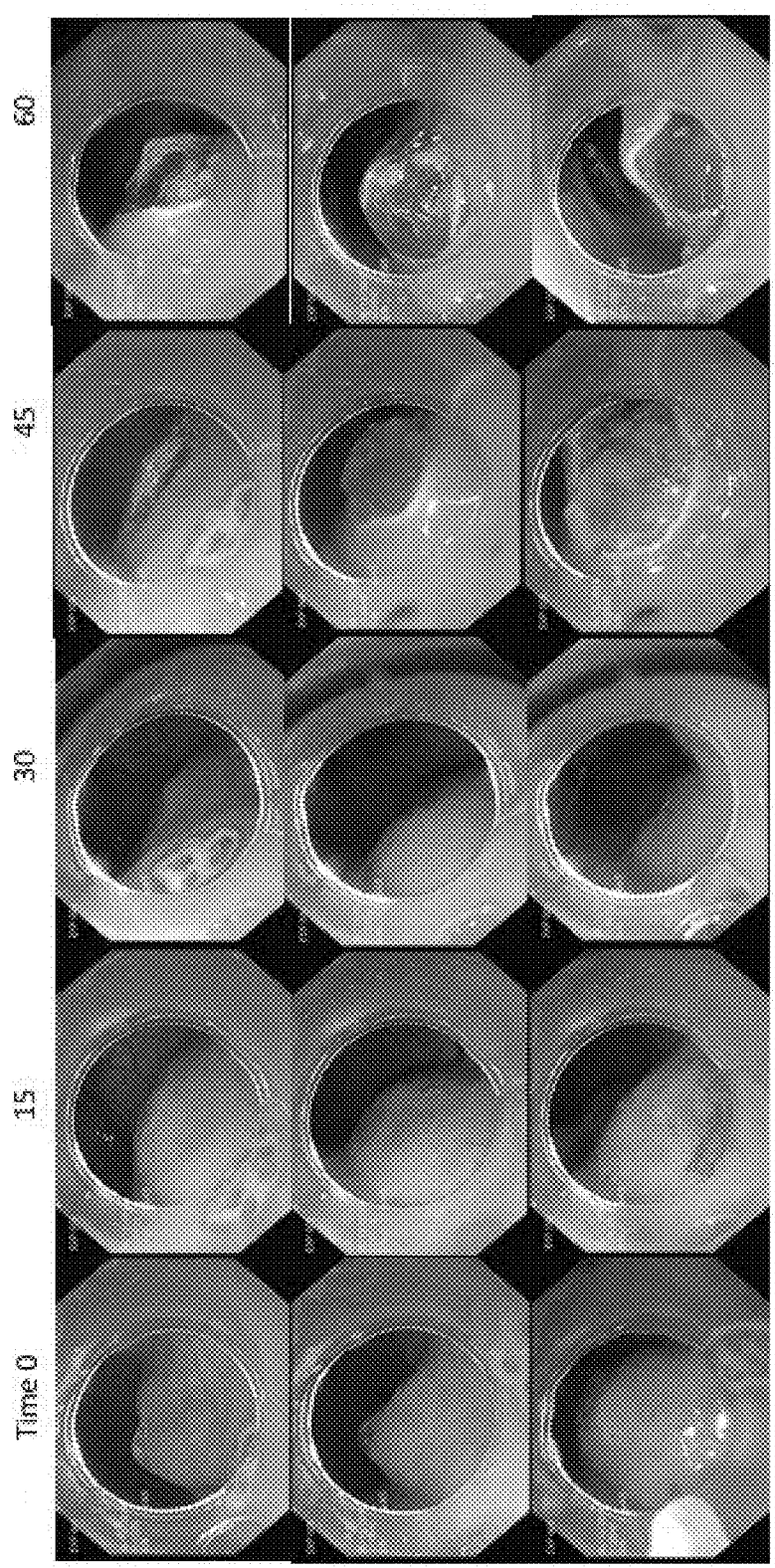

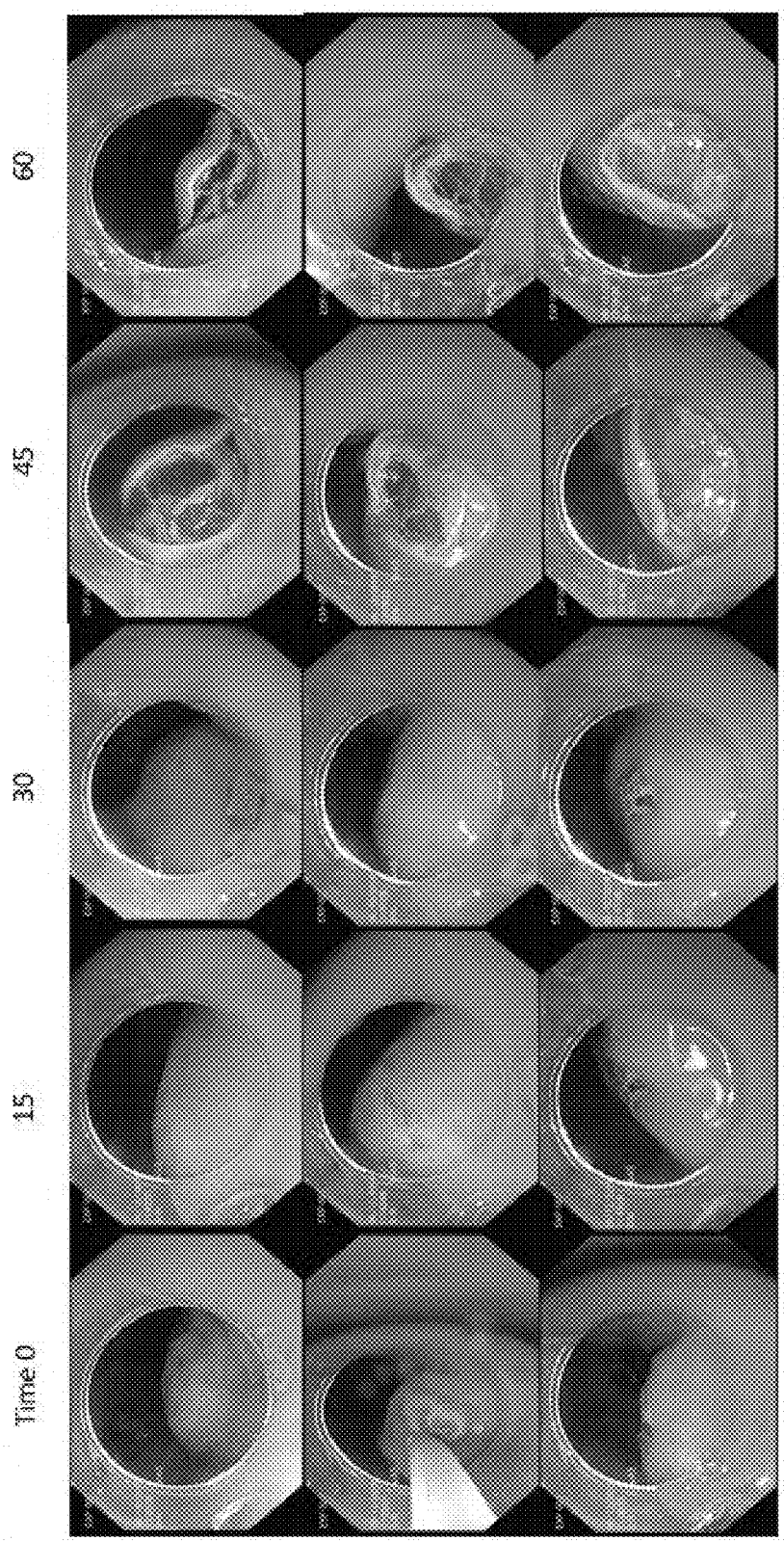

HYDROGEL COMPOSITION FOR MUCOSAL LIFTING PROCEDURES WITHIN LUMENAL ANATOMICAL STRUCTURES

CROSS REFERENCE TO RELATED APPLICATIONS

This application is a continuation of U.S. patent application Ser. No. 17/415,775, titled "Hydrogel Composition for Mucosal Lifting Procedures within Lumenal Anatomical Structures," filed Jun. 18, 2021, now U.S. Patent Application Publication No. 2022/0062498 which is a U.S. National Stage Entry of International Patent Application No. PCT/US2019/067966, titled "Hydrogel Composition for Mucosal Lifting Procedures within Lumenal Anatomical Structures," filed Dec. 20, 2019, which claims priority to U.S. Provisional Application No. 62/784,213, titled "Hydrogel Composition for Mucosal Lifting Procedures within Lumenal Anatomical Structures," filed Dec. 21, 2018, the entirety of which is incorporated by reference herein.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The current invention relates to injectable hydrogel formulations. More particularly, the present invention relates to formulations that contain hydrogel particles that form networks within certain temperature ranges.

BACKGROUND

Gelation is a complex process, and attempts to theoretically quantify this have been attempted previously. During polymerization (gelation), up to an infinite number of networks are produced. The key issue in this process is bond formation, which in turn causes cluster formation. The more clusters that are formed, gelation occurs. If p corresponds to the probability of bond formation, pc corresponds to the gel point. When p>pc, at least one infinite polymer cluster appears, and a lattice appears. This process is called percolation. Examples of real experimental parameters that affect the probability of bond formation include temperature, pH, concentration, polymer reaction extent, polymer-polymer interactions, polymer-solvent interactions, polymer-co-solvent interactions, and polymer-additive interactions.

Hydrogels exhibit a relatively large change in volume pertaining to a small change in external stimuli, e.g., temperature, due to the formation of hydrogel polymer networks, which in turn cause polymer swelling.

Numerous clinical circumstances may gain significant advantage from the injection of hydrogel formulations. For example, the technique of gastrointestinal submucosal injection—lifting the overlying mucosa or "mucosal lift"—involves the therapeutic introduction of hydrogel formulations into the submucosal space of the intestine. The submucosa is a potential space between the superficial mucosal and deeper muscle layer of the intestine, for example, to either raise a mucosal lesion away from the muscle layer to aid in lesion removal or to mark the intestine by depositing a pigment in the intestinal wall to identify a particular location. Long lasting, non-dissipating lifting (e.g., by a hydrogel formulation) is desirable for managing various diseases, disorders and conditions. In fact, any lumenal structure, i.e. any anatomical structure with a central lumen and a multi-layered wall, could benefit from such an agent (e.g. lung, urological and gynecological).

In a typical mucosal lifting procedure that includes injection of the formulation into the submucosal space to lift the mucosa away from the deeper muscle wall (see FIG. 1), an endoscope is first inserted into the patient's mouth or anus and navigated to the area of interest. The area of interest may include, but is not limited to, a site of pathological abnormality, e.g., adenomatous polyps or a site of previous pathology, e.g., where a previous surgical procedure was performed. The area around the abnormality is then mucosally punctured using a long needle injector catheter, typically over two meters in length, which is placed inside the endoscope working channel.

The hydrogel formulation is transferred into the submucosal space under the lesion, typically via depressing a syringe plunger in which the hydrogel formulation is loaded. Appropriate lifting of the pathology is confirmed visually by the clinician, typically through the lifting of the mucosa. This lifting adds a degree of safety for surgical removal of the lesion by providing a "cushion" or "bleb," i.e., a separation of the mucosal surface and the muscle wall, thus reducing the risk of perforation, i.e., breach of the muscle layer of the intestine and subsequent passage of fecal contents inside the peritoneal surface of the patient. The peritoneal surface is sterile, thus contamination with fecal contents is typically catastrophic.

In a typical marking procedure, at the area of interest either proximally or distally and either prior to or after the lifting procedure, the submucosal space is again injected (this time with a submucosal injection formulation that loaded with pigment). The marking formulation and pigment are then deposited through the long endoscopic needle injector catheter.

The type of mucosal lifting formulation is chosen, for example, based on the size of the pathology, location of pathology within the gastrointestinal tract, and whether or not electrocautery will be used. Electrocautery refers to the use of electrical energy to either incise or cauterize the tissue. Further, the submucosal marking formulation is chosen based on whether the clinician wishes to mark the intestinal area for referral of the patient to another clinician or whether that same clinician wishes to re-examine the patient at a later date to determine cure or recurrence of the pathology.

Various non-polymer based and polymer-based mucosal lifting and marking formulations are currently employed in clinical practice. These formulations are typically introduced to the location of the intended lifting or marking through long needle catheters, such as needle catheters up to 240 cm long and between 22-25 gauge in diameter. Due to the long length and small diameter of the long endoscopic needle catheter, usable lifting and marking agents are typically Newtonian in behavior i.e. liquid-like. The materials that have been used commercially for lifting procedures include 0.9% normal saline (sodium chloride dissolved in water for injection), 6% hydroxyethylstarch (e.g. Hetastarch™).

Similar Newtonian fluids have been used in mucosal lifting procedures to increase the formulation submucosal residence time after delivery, i.e., to reduce dissipation. For instance, human albumin solution and dextrose solution have been used as mucosal lifting agents by employing higher solution osmolality and thus theoretically retaining water in the submucosal space for longer periods of time. The difficulty with this approach is the observation that the mucosal lift is not durable due to rapid dissipation, reducing the degree of mucosa lift and increasing the risk of muscle perforation. Injected submucosal agent rapid dissipation also requires multiple repeated injections of the agent by the clinician which increases the procedure time and cost. In the case of marking agents, such as India ink (SPOT™, GI supply) and methylene blue, dissipation of the agent leads to inaccurate marking and sometimes disappearance of the marking pigment all together.

In an attempt to improve the lifting durability of the mucosal lifting agent and decrease the rate of dissipation, agents with increased viscosity have been used, e.g., hyaluronic acid and methylcellulose. However, problems have been encountered pertaining to the high injection forces required to pass highly viscous agents within the long, narrow endoscopic needle injector catheters. It is also known that polymer-based purified or microemulsion agents for lifting procedures (e.g. LeGoo-Endo™ or Eleview™) have been used. However, these agents exhibit Newtonian behavior within parameters inside of the ideal required operative range, i.e. these agents exhibit liquid characteristics up to 40 degrees Celsius, which is significantly above normal physiological body temperature of 37 C. Eleview™ also exhibits several undesirable characteristics in the field of adenomatous polyp removal, such as leakage of the agent upon electrosurgical incision, thereby hampering the clinician's view of the procedure.

Therefore, the current state of the art has clear limitations and can be summarized by the following:
1. Rapid dissipation, i.e., rapid absorption of the agent into the surrounding tissues over time decreasing mucosal lift (or dome height), corresponding to decrease of the submucosal 'cushion' or 'bleb'.
2. Poor marking pigment accuracy (related to fast dissipation)
3. Leakage of agent when performing therapeutic procedures, e.g., incision to the intestinal mucosa using electrosurgery causes the agent to leak out of the submucosal space
4. Bubbling of agent when electrosurgery is applied, leading to impaired view of the surgical operating field.
5. High injection forces required to inject viscous fluid along long endoscopic needle injectors (up to 240 cm in length and less than 0.5 mm in diameter), rendering single handed operation impossible.

A mucosal lifting agent that addresses some or all of these limitations is therefore desired.

SUMMARY OF THE DISCLOSURE

Described herein are hydrogel compositions that are temperature sensitive and can be made of a hydrogel (i.e., a natural or synthetic network of polymer chains that are strongly hydrophilic (containing up to 99.9% water)). The hydrogels can have a low viscosity while passing through the catheter to make it easier for the physician or healthcare provider to apply force to the syringe by hand to deliver the hydrogel to the target location. Further, the increase in temperature of the hydrogel upon injection into the body can result in an increased viscosity when placed in the submucosal wall. The increased viscosity can allow the hydrogel to stay within the injection site for a longer period of time, thereby improving the efficiency of the surgical procedure (multiple injections may not be required as is required with the prior art compositions).

In general, in one embodiment, an injectable medical composition includes an acrylate and a solvent. The composition has a first viscosity at temperatures below body temperature and a second viscosity at body temperature. The first viscosity is lower than the second viscosity.

This and other embodiments can include one or more of the following features. The composition can be configured to be in a Newtonian state at temperatures below body temperature and in a non-Newtonian state at body temperature. The acrylate can include a poly(acrylic acid) copolymer. The poly(acrylic acid) copolymer can include allyl sucrose or allyl pentaerythritol. The composition can further include poly(ethylene oxide)-b-poly(propylene oxide)-b-poly(ethylene oxide). The acrylate in the composition can be between 1.9% and 02.5% w/v. Body temperature can be 35.5° C.-38.5° C. The second viscosity can be less than 4 Pa·s at shear rates of up to 10 s−1. The second viscosity can be greater than 0.2 Pa·s at shear rates of up to 10 s−1. The second viscosity at a shear rate of 10 s−1 can be at least 30% less than the second viscosity at a shear rate of 1 s−1. A shear stress of the composition at body temperature can be less than 100 Pa at a rate of 0.1 s−1. A hardness of the composition at body temperature can be between 1N and 10N. An adhesiveness of the composition at body temperature can be less than 10N. A compressibility of the composition at body temperature can be less than 10N. An elasticity of the composition at body temperature can be less than 10N. A maximum mucosal detachment force of the composition at body temperature can be less than 5N. A mucoadhesion force of the composition at body temperature can be less than 5 mJ/cm2. A work of adhesion of the composition at body temperature can be less than 5N. The composition can be configured to generate a mucosal lift when injected submucosally, and the mucosal lift can retain over 60% of its original height for over 60 minutes. Contents of a 5-10 cc syringe filled with the composition can be deposited within the submucosal space through an endoscopic needle injector, using less than 20 Kg force in less than 90 seconds. The viscosity of the composition can be less than 800 mPa·s at 22° C. and greater than 2500 mPa·s at 37° C. The composition, after injection submucosally, can be configured to limit a transference of electrical energy to a deeper intestinal wall when electrosurgery is applied. The viscosity of the composition can reduce to less than 100 mPa·s within 90 minutes of injection submucosally. The composition can exhibit a G' value of greater than 7000 Pa·s between 0.1-10.0 Hz at body temperature. The composition can exhibit a G" value of greater than 1300 Pa·s. between 0.1-10.0 Hz at body temperature. The composition can be manufactured by mixing components thereof at a temperature less than 10° C. The composition can be manufactured by sequentially adding polymers to the solvent under magnetic stirring at less than 250 rpm. The composition can be manufactured by pre-mixing polymers at 100 rpm for 1 minute prior to addition to addition of the solvent to affect the final viscosity. The injectable medical composition can further include polystyrene or other microspheres at a concentration of 4.2%. The composition with the polystyrene or other microspheres can have a viscosity that is 12% higher than a composition without the polystyrene or other microspheres. The injectable medical composition can further include a marking pigment. The marking pigment can allow for visible identification of the composition upon injection for up to 60 days. The polymer may not include poly (propylene oxide). The polymer may not include poly(ethylene oxide). The composition may not include an oily component. Polymers can include about 1% to about 10% of the composition by weight. Polymers can include about 2% to about 4% of the composition by weight. The solvent can include distilled water. The solvent can include carbonic acid or sodium acetate. A pH of the composition can be approximately 5.1-7.4. The injectable medical composition can further include a coloring agent. The coloring agent can be a dye. The dye can be methylene blue.

In general, in one embodiment, a method of performing a surgical procedure at a surgical site in mucosal tissue includes (1) injecting an aliquot of a hydrogel composition to raise an outer mucosal layer of the mucosal tissue a distance away from a submucosal layer at the surgical site, (2) maintaining the outer mucosal tissue layer at least 60% of the distance away from the submucosal layer for at least one hour, and (3) performing the surgical procedure on the outer mucosal layer during the maintaining step.

This and other embodiments can include one or more of the following features. The injecting step and performing step can be performed endoscopically. The hydrogel can have lower viscosity at a first temperature and higher viscosity at a second temperature where the first temperature is lower than the second temperature. The first temperature can be room temperature (which can have a temperature range of approximately 20 to 25 degrees Celsius), and the second temperature can body temperature (which can have a temperature range of approximately 35.5 to 38.5 degrees Celsius). Injecting an aliquot can further include maintaining the outer mucosal tissue layer at least 90% of the distance away from the submucosal layer for at least 90 min. The aliquot can have a volume of about 20 ml or less.

In general, in one embodiment, a method of performing a surgical procedure at a surgical site in mucosal tissue includes (1) injecting an aliquot of an hydrogel composition to raise an outer mucosal layer of the mucosal tissue a distance away from a submucosal layer of the mucosal tissue at the surgical site where he hydrogel composition has lower viscosity at a first temperature and higher viscosity at a second temperature, the first temperature being lower than the second temperature, (2) maintaining the distance for at least 90 min, and (3) performing the dissection on the outer mucosal layer.

This and other embodiments can include one or more of the following features. The first temperature can be room temperature having a temperature range of approximately 20 to 25 degrees Celsius and the second temperature is body temperature having a temperature range of approximately 35.5 to 38.5 degrees Celsius. Wherein the distance is maintained for at least four hours.

In general, in one embodiment, a method of using a hydrogel composition as a marking agent in surgical procedure includes (1) injecting an aliquot of a hydrogel composition at a surgical site to visually distinguish the surgical site from surrounding tissue, where the hydrogel composition has lower viscosity at a first temperature and higher viscosity at a second temperature and where the first temperature is lower than the second temperature, (2) maintaining visual delineation of the surgical site for at least 90 minutes, and (3) performing the procedure at the surgical site. The hydrogel composition includes a polymer composition and a coloring agent.

This and other embodiments can include one or more of the following features. The first temperature can be room temperature having a temperature range of approximately 20 to 25 degrees Celsius and the second temperature is body temperature. Wherein the hydrogel composition provides visual delineation for at least four hours.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 13A-13O show the lifting of various hydrogel formulations relative to controls at 0 min, 15 min, 30 min, 45 min, and 60 min.

DETAILED DESCRIPTION

Described herein are injectable formulations (also referred to herein as "hydrogel" or "hydrogel formulation") that contain temperature-sensitive hydrogel particles. The hydrogel may exhibit Newtonian behavior below normal body temperature and/or may exhibit non-Newtonian (viscoelastic/gelling) behavior above normal body temperature. Such injectable formulations can be used, for example, in conjunction with endoscopic medical procedures to act as mucosal lifting agents. Thus, the mucosal lifting agents can exhibit Newtonian behavior at temperatures less that 37° C. and exhibit non-Newtonian behavior at temperatures at or above 37° C.

The hydrogels described herein can be endoscopically injected into the submucosal space, elevating mucosally based lesions away from the underlying layers of the intestinal wall and introducing a margin of safety for lesion removal. The hydrogels can advantageously provide enough separation of the layers for a sufficient time for the endoscopic procedure to be performed. Additionally, the hydrogels described herein can advantageously maintain their shape during the entire or nearly the entire procedure. The hydrogels described herein can act as marking and cushioning agents that are safe and provide long-lasting separation without diffusing into the surrounding areas. Additionally, the hydrogels can be easily transferred from an injection device (e.g., a syringe) to the treatment site. In some embodiments, the hydrogels are less viscous at ambient temperatures than at body temperature. Additionally, the hydrogels can remain in the less viscous state as they travel from the injection device to the treatment site so that the entirety of the hydrogel formulation may be delivered to the subject prior to a change in viscosity of the composition.

The hydrogel formulations having Newtonian characteristics below the normal body temperature can be injected into the body of a subject. Subjects can include vertebrate subjects, particularly humans and various animals including pigs. By injecting the hydrogel formulation into the body at a temperature that is below that of the Newtonian to non-Newtonian change temperature, the formulation may be injected into the subject in a constricted morphology. Upon warming in the body to physiological temperature, however, the polymers can become agitated, for example, increasing the likelihood of bond formation, or network formation, ultimately producing non-Newtonian characteristics.

Figure 3:
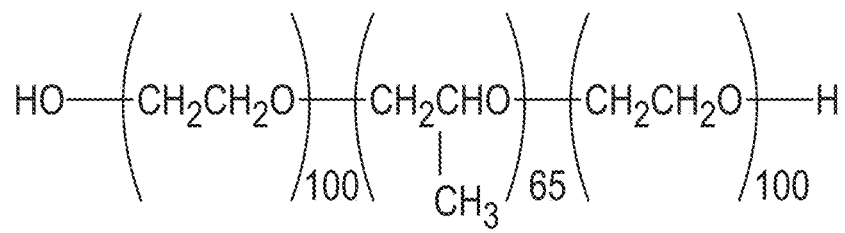
FIG. 3 shows the chemical structure of a PEO-PPO-PEO triblock copolymer.

The hydrogel formulations described herein can include acrylates and/or poloxamers (homopolymers and block copolymers, respectively), both of which can advantageously alter their swelling upon change of temperature. In one exemplary embodiment, the hydrogel formulation includes poly(acrylic acid) (PAA) copolymers modified with block-copolymers of poly(ethylene oxide) (PEO) and poly(propylene oxide) (PPO). For example, poly(acrylic acid) can be bonded onto a PEO-PPO-PEO triblock (e.g., Pluronic®) backbone via dispersion polymerization. The chemical structure of a PEO-PPO-PEO triblock copolymer is shown in FIG. 3. Initial optimization of the synthesis can define appropriate levels of initial loading of acrylic acid and PEO-PPO-PEO triblock copolymer, with a mixture of 2,2'-azobis(2,4-dimethylpentanenitrile) and lauroyl peroxide as an initiator system. The synthesis can result in a copolymer with low residual monomer content and a very high degree of bonding between PEO-PPO-PEO triblock copolymer and PAA. Diluted aqueous solutions of PEO-PPO-PEO triblock copolymer-g-PAA exhibit rapid thermogelation.

Figure 1:
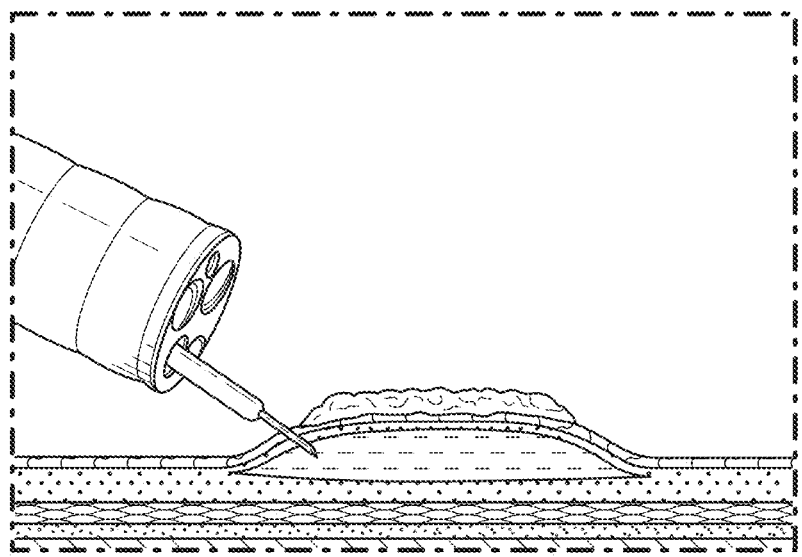
FIG. 1 shows injection of an agent into the submucosal space of the intestine via an endoscopic needle injector catheter passed through the working channel of the endoscope.
Figure 2:
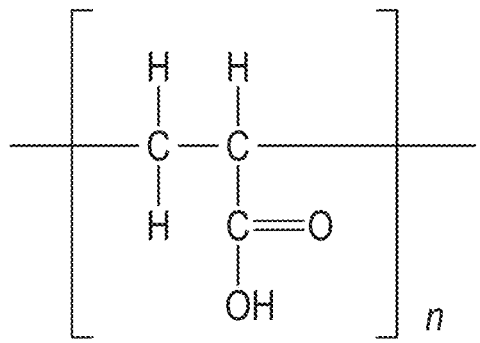
FIG. 2 shows the chemical structure of a carbomer.

In some embodiments, the hydrogel formulations described herein can include a carbomer, such as Carbopol®. Carbomers are synthetic high-molecular-weight polyacrylic acids cross-linked with allyl sucrose or allyl pentaerythritol and contain between 56 and 68% w/w carboxylic acid groups. The chemical structure of a carbomer is shown in FIG. 2. In some embodiments, the hydrogel formulations can additionally include a non-ionic triblock copolymer of poly(ethylene oxide)-b-poly(propylene oxide)-b-poly(ethylene oxide) (PEO-PPO-PEO), such as Pluronic® poloxamer.

In some embodiments, the hydrogel compositions described herein can be administered within the submucosal space of the human intestine, such as for removal of a polyp via Endoscopic Mucosal Resection (EMR) or Endoscopic Submucosal Dissection (ESD). Exemplary procedural steps to deposit the disclosed hydrogel formulation(s) into the submucosal space of the human intestine are as follows. A 5 cc-10 cc syringe (equipped with a luer lock) can be filled with the hydrogel formulation and capped and sterilized ("the device"). The device can be opened and connected to a commercially available endoscopic needle injector via the luer connector (e.g., a 240 cm, 2.8 mm diameter catheter with a 22-25 G needle at its tip). The needle injector can be primed with the device, i.e., by injecting up to 2 cc within the catheter so that hydrogel formulation appears at the needle tip. The needle injector tip can be deployed into the location where the device is to be injected i.e. the submucosal space. Upon appropriate location, the operator or operating assistant can depress the syringe plunger to inject less than 1 cc of the hydrogel formulation to confirm placement. After positive confirmation from the operator, the desired amount of hydrogel formulation can be injected into the submucosal space. After injection is completed, the needle can be resheathed into the catheter and the endoscopic needle injector removed from the endoscope in it's entirety. The device syringe can then be disconnected from the needle injector. The entire device can be disposed of.

The hydrogels described herein can advantageously be used for injection-assisted EMR and can be safe, inexpensive, non-toxic, readily available, easy to inject and capable of providing a high, long-lasting submucosal cushion. In some embodiments, the hydrogels can be colored (e.g., with a dye) that can aid with distinguishing more easily the depth of the muscolaris mucosa, thereby avoiding undue perforation during techniques such as ESD. In some embodiments, the pigment can include methylene blue or FDandC #1. The amount of pigment can be, for example, less than 20 cc, such as less than 10 cc, such as approximately cc of 1% pigment per 100 cc of solution. Keeping the amount of pigment (e.g., methylene blue) low can increase the thermosensitive effects of the hydrogel.

The hydrogels described herein can have minimal diffusion within the intestinal walls, resulting in sustained height of the mucosal lesion away from deep layers and maintaining 75%-100%, such as 90%-100%, of its original height over a reasonable amount of time. Further, the hydrogels can be non-toxic but also biocompatible and can produce little or no local or systematic side effects. The hydrogels can be configured so as to not conduct heat or electricity, which may interfere with the endoscopic procedure being performed. Further, the hydrogels can be easy to handle at or below room temperature and can be of sufficiently low viscosity to be injected over a long endoscopic delivery system (e.g. greater than 220 cm). The hydrogels described herein can be highly compatible with therapeutic flexible endoscopies (FE) and can improve patient outcomes by reducing risk and speeding up recovery times, particularly for patients with benign diseases that would otherwise require major traditional surgery.

In use, the hydrogels described herein can advantageously expand the submucosal layer of the intestinal where the mucosa is elevated away from underlying layers of the intestinal wall and bulges into the intestinal lumen, permitting better visualization of a lesion and enhanced options for removal or sampling of pathology.

In some embodiments, the hydrogel compositions described herein can include one or more of the following features:
1. The formulations can retain 50-90%, such as approximately 60% of the original injected dome height 1 hr after injection.
2. The formulations can be delivered via an off the shelf syringe. The contents (e.g., up to 5-10 cc and/or a needle of at least 100 cm or 25 G) can be expelled into the submucosal space within 90 seconds using up to 20 Kg force.
3. The formulations can have a viscosity of approximately 800 mPa·s at 22° C. and approximately 2500 mPa·s at 37° C.

4. The formulations can have a hardness when injected into the submucosal space at 37° C. that exceeds 1N (e.g., is between 1N and 10N).
5. The formulations can have a mucoadhesion that exceeds 5 mJ/cm2 at 37° C.
6. The formulations may not produce excessive bubbles when electrosurgery is applied.
7. The formulations may reduce to less than 100 mPa·s within 90 minutes of injection.
8. The formulations can dissipate within 360 minutes at 37° C.
9. The formulations may exhibit a G' greater than 7000 Pa·s and a G" greater than 1300 Pa·s.
10. The formulations can include a pigment that permits identification of the injected area in addition to the anatomical structures of the submucosal space.

In some embodiments, the hydrogel compounds described herein may include additional bio-compatible agents. For example, in some instances, a therapeutic agent may be included. By way of example only, therapeutic agents may include a non-steroidal anti-inflammatory agent, a steroid, an analgesic, or an antimicrobial agent. In other examples, the hydrogel composition may include an anesthetic.

The hydrogels described herein can include a small percentage of a polymer or hydrogel (e.g. a carbomer and PEO-PPO-PEO triblock copolymer). In some instances, the hydrogel composition includes 0.2%, 0.3%, 0.4%, 0.6%, 0.8%, 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, or 5% of a carbomer, such as Carbopol ETD. In other variations, the hydrogel composition includes 0.2%, 0.3%, 0.4%, 0.6%, 0.8%, 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, or 5% of a carbomer, such as Carbopol NF. In yet other examples, the hydrogel composition may include 10%, 12%, 14%, 16%, 18%, 20%, 22%, 24%, 26%, 28%, 30%, 32%, or 34% PEO-PPO-PEO triblock copolymer, such as Pluronic 127. In some other variations, a combination of various hydrogels may be used. For example, a combination of a carbomer and PEO-PPO-PEO triblock copolymer may be used. The combination of a carbomer and PEO-PPO-PEO triblock copolymer may be 0.2% and 14%, 0.3% and 14%, 0.4% and 14%, 0.2% and 13%, 0.2 and 15%, 0.4% and 14%, 0.6% and 14%, 0.3% and 13%, 0.3% and 15%, 0.3% and 28%, 0.3% and 27%, 0.3% and 29%, 0.4% and 27%, 0.4% and 28%, 0.4% and 29%, 0.5% and 27%, 0.5% and 28%, 0.5% and 29%, 0.6% and 27%, 0.6% and 28%, or 0.6% and 29% respectively.

The hydrogel formulations described herein can include any suitable carbomer or PEO-PPO-PEO triblock copolymer agent depending on the desired hydrogel formulation characteristics. These include, but are not limited to, Poloxamer 188, Carbopol 971P NF, Carbopol 974P NF, Carbopol AA-1 and Carbopol ETD2020. The concentrations of the aforementioned polymers and co-polymers can range within the limits of 1, 2, 5, 10, or 20 to 30 g/100 mL of solvent and co-solvent. In addition, the concentrations can range 0.01, 0.01, 0.5 to 0.9 per 100 mL.

In some embodiments, a buffer may be used to stabilize the polymer components and or/solution components. Such buffers may be, for example, carbonic acid or sodium acetate buffer solution. These buffers can, for example, help stabilize the solution when electrosurgical tools are used.

In one exemplary embodiment, the hydrogel can include poloxamer (5%), carbomer (2.5%), xanthum gum thickener (1%), sterile water (74%), pigment (1%) and a buffer (25%).

A plurality of exemplary hydrogel formulations and their methods of manufacture are described herein.

Experimental Study 1

In a first experimental study, a hydrogel formulation as described was produced and its characteristics (e.g., gel transition temperature, flow deformation, viscosity, storage modulus, loss modulus, hardness, mucoadhesion, conductivity, and dome height) analyzed. The hydrogel formulation included 50 mL of water, 1 g of Poloxamer 407, 0.1 g of carbomer (Carbopol 971P), and 0.001 g of methylene blue. In a first embodiment (formulation A), the poloxamer and carbopol were sequentially mixed. In a second embodiment (formulation B), the poloxamer and carbopol were pre-mixed. The method of producing the hydrogel formulation included:

1) In a stainless steel or other suitable vessel provided with a suitable stirrer, (the stirrer weighed 5.88 g per 100 cc), at 50-100 rpm, 50 mL of water for injection was loaded. Then, 50 mL of sodium chloride was added. The mixture was kept under constant temperature control between 3 to 10° C. Then, 1 g of Poloxamer 407 was added under stirring until completely submerged. Then 0.1 g of Carbopol 971P was added until completely submerged. The mixture was kept under stirring for 1 hour. This is termed sequential mixing (formulation A); or In a stainless steel or other suitable vessel provided with a suitable stirrer at 50-100 rpm, 50 mL of water for injection was loaded. Then, 50 mL of sodium chloride is added. The mixture was kept under constant temperature control between 3 to 10° C. Then, 1 g of poloxamer 407 is mixed with 0.1 g of Carbopol 971P at 10 rpm-100 rpm for 5 minutes. The resulting mixture was then added to the water and sodium chloride mixture. This is termed pre-mixing (formulation B).
1) The mixture was then removed from the temperature controlled stirrer and placed in refrigeration 4° C. for 24 hrs.
2) The mixture of step (2) was then warmed to 22° C. (room temperature).
3) The pH of the mixture was measured and it is brought, if necessary, within the range 4.0-8.0, such as 5.0-7.5, such as 5.1-7.4 through addition of sodium hydroxide 0.01M.
4) After this, 0.001 g of methylene blue was added under stirring. The mixture was kept under stirring until homogeneity at 50-100 rpm.
5) The final composition was filtered through a 0.40 μm filter and packed in 5 cc syringes and capped. The syringes (and formulation therein) were sterilized with Ethylene oxide sterilization (ETO), electron beam sterilization, or other methods of sterilization.

The hydrogel formulation was characterized based upon solution gelation transition temperature (SGTT), flow and deformation characteristics, viscosity change over time under physiological conditions, the elastic modulus or loss modulus, mechanical properties (e.g., hardness, compressibility, cohesiveness, retraction force), adhesive force, electrical conductive properties, performance upon addition of microbeads, degree of mucosal lift, pigment marking, electrical conduction upon application of electrosurgical energy, and pigment injection accuracy over time. The experimental results pertaining to each of these characteristics are summarized below.

The first characteristic analyzed was the Solution (Sol) Gelation (Gel) Transition Temperature (SGTT) of the hydrogel formulation. SGTT can be used as a key parameter in defining the clinical suitability of a hydrogel formulation compositions as disclosed herein. At SGTT, the properties of the hydrogel formulation change from a liquid-like state (Newtonian) to a solid-like state (non-Newtonian), which corresponds to significant viscosity increase and mucosal lift. Advantageously, if the hydrogel formulation can reach SGTT at 37° C.+/−1.5, a robust lift will be gained upon the formulation reaching body physiological temperature.

To analyze the SGTT, a magnetic temperature controlled stirring plate was used (TECA AHP-301MSP), allowing computer controlled accurate temperature modulation. In this case, a temperature ramp from 4 to 45° C. was used, where the plate was set to increase the temperature by 1 C per minute. A 4.75 g stirrer bar was placed in the bottom of either a 100 or 50 cc beaker and set to 100 rpm. The temperature at which the stirrer bar stopped was considered the formulation SGTT. Normal saline and Eleview™ (a commercially available poloxamer emulsion) were used as reference agents in this testing.

SGTT results of the formulations compared to reference agents are shown in Table 1 below. As indicated, normal saline and Eleview™ do not reach gelation viscosity at physiological temperatures, whereas the formulation compositions disclosed herein gel at physiological temperatures+/−1.5° C.

TABLE 1

| SGTT | |
| --- | --- |
| Agent | SGTT (° C.) |
| Normal Saline | >45 |
| Eleview ™ | >45 |
| Hydrogel formulation (A) | 35.8 |
| Hydrogel formulation (B) | 37.9 |

The second characteristic analyzed was the flow and deformation of the hydrogel formulation (with focus on absolute viscosity). The in-vitro hydrogel formulation viscosity determination can provide key information regarding hydrogel resistance to gradual deformation by shear or tensile stress. For liquids, it corresponds to the informal concept of "thickness," e.g. honey's viscosity is higher than that of water. This data can give important information regarding the viscosity changes exhibited by the formulations through external stimuli changes, e.g., changes to viscosity according to temperature change. Viscosity is a property which opposes the relative motion between two surfaces of the fluid moving at different relative velocities. In simple terms, viscosity designates the friction concerning the fluid molecules. When fluid is forced through a tube, the fluid composition particles generally move faster near the tube's axis and slower near its walls. Therefore, some stress (such as a pressure difference between the two ends of the tube) is needed to overcome the friction between particle layers to keep the fluid moving. For a given velocity pattern, the stress required is proportional to the fluid's viscosity. In this situation, a formulation with a viscosity similar to water at room temperature and changing to a higher viscosity at body temperature would be advantageous. This would be clinically relevant, as it indicates the formulation would be injectable along the long thin endoscopic needle injector catheters and subsequently increase its viscosity once in the submucosal space of the hydrogel intestine (and exposed to body temperature), thus providing a durable mucosal lift, through reducing the probability of dissipation. Table 2 below shows typical viscosity values.

TABLE 2

| Viscosity Values | |
| --- | --- |
| Materials | Viscosity (Pa · s) |
| Air/Gas | 0.00001 |
| Water | 0.001 |
| Milk/Coffee | 0.01 |
| Olive oil | 0.1 |
| Glycerol | 1 |
| Liquid Honey | 10 |
| Molasses | 100 |
| Polymer Melt | 1000 |
| Asphalt Binder | 100,000 |

To analyze flow and deformation, rheological analysis of the hydrogel formulation were performed at 22±0.1° C. and 37±0.1° C. using an AR 2000 controlled stress/controlled rate rheometer (TA instruments, New Jersey, USA), in flow mode, and in conjunction with parallel steel plate geometry (40 mm diameter). In continuous shear analysis, upward and downward flow curves for each formulation were measured over shear rates ranging from 1-$10^5$ s$^{-1}$. Oscillatory analysis of each formulation under examination was performed after determination of its linear viscoelastic region at 22±0.1° C. and 37±0.1° C., where stress was directly proportional to strain and the storage modulus remained constant. Frequency sweep analysis was performed over the frequency range of 0.1-10.0 Hz following application of a constant stress and standard gap size was 0.1 mm for each sample. Normal saline (Baxter, Deerfield, Ill.) and Eleview™ (Aries Pharmaceuticals, CA, USA) were used as reference agents.

Figure 4:
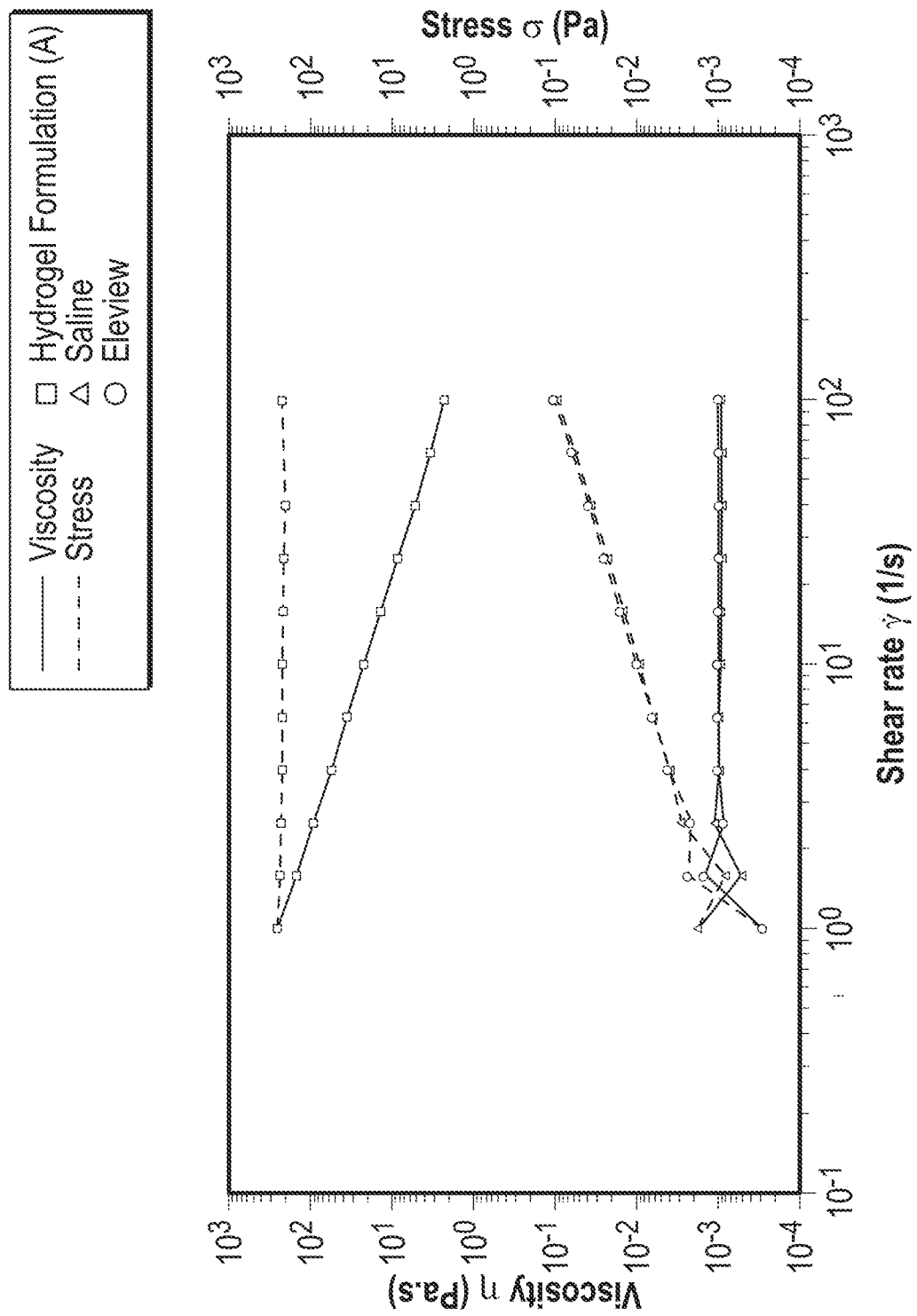
FIG. 4 shows results of a flow sweep analysis for a hydrogel formulation relative to controls.

The resulting viscosity (based upon logarithmic flow sweep analysis) is shown below in Table 3 and in FIG. 4.

TABLE 3

| Viscosity relative to Temperature | | |
| --- | --- | --- |
| Agent | Viscosity (mPa · s) @ 22° C. | Viscosity (mPa · s) @ 37° C. |
| Normal Saline | 1.22 | 0.9 |
| Eleview ™ | 6 | 3.8 |
| Hydrogel formulation (A) | 164 | 22022 |

All agents exhibited Newtonian (liquid) behavior at 22° C. Only the hydrogel formulation disclosed herein, however, exhibited a viscosity change at 37° C. (i.e., exhibited a significantly higher viscosity, such as 10 times or more, 50 times or more, 100 times or more, or 125 times or more higher, at 37° C. relative to 22° C.). This viscosity change is important to ensure that the hydrogel formulation remains in place during a procedure, such as mucosal lifting. In contrast, those formulations with viscosities at the same level as saline (e.g., substantially consistent from 22° C. to 37° C.) would be expected to dissipate rapidly and so perform poorly as a mucosal lifting agent.

The third characteristic analyzed was viscosity change over time under physiological conditions to simulate the submucosal space residence time of the hydrogel. Determination of the in-vitro rheological properties of the hydrogel over time offers key information regarding hydrogel formulation behavior after deposition into the chosen anatomical area, e.g., after injection into the submucosal space of the intestine. A formulation with a viscosity that decreases over time to that of something akin to saline over 60-90 minutes would be advantageous, as this indicates the formulation would provide a durable mucosal lift for the typical procedure time, reducing the need for repeat injections and risk of perforation of the muscle layer. This level of submucosal residence time also ensures that the hydrogel formulation is not be permanent and would therefore will not obstruct the intestinal lumen.

Figure 5:
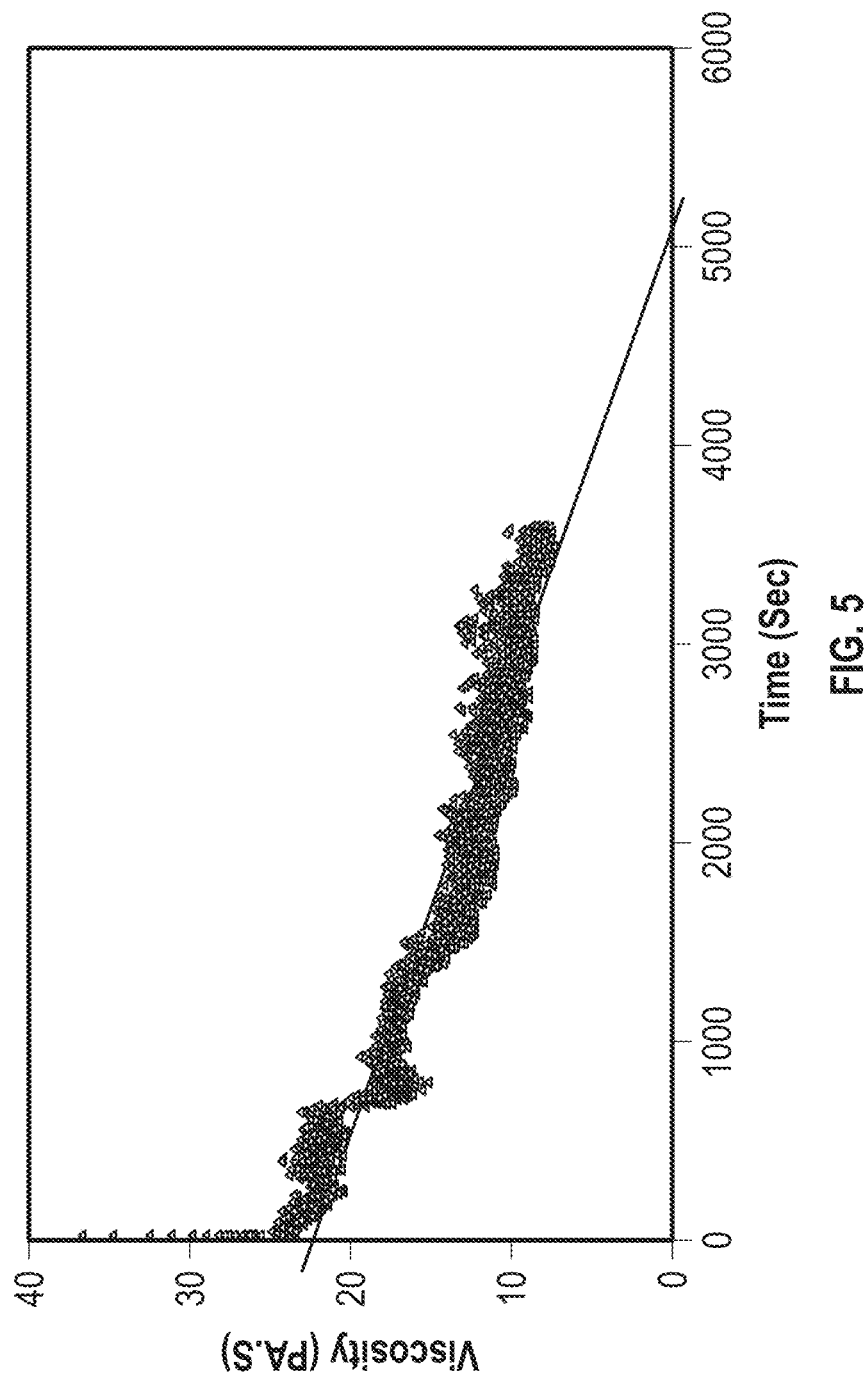
FIG. 5 shows results of viscosity analysis for a hydrogel formulation over 1 hour at 37° C. under constant shear rate of 10/s to simulate submucosal space.

To analyze the viscosity change over time, the hydrogel formulation was rheologically analyzed at 37±0.1° C. using an AR 2000 controlled stress/controlled rate rheometer (TA instruments, New Jersey, USA), in flow mode, and in conjunction with parallel steel plate geometry (40 mm diameter). Viscosity was measured over 60 minutes under a constant shear rate of 10/s (simulating the submucosal space). The viscosity decay over time is shown in Table 4 below and in FIG. 5. As shown, the formulation advantageously dissipates to a viscosity similar to saline in approximately 85 minutes.

TABLE 4

Viscosity relative to Temperature

| Agent | y-intercept-viscosity (mPa · s) | x-intercept-time to reach 0 viscosity (seconds) | R2 |
|---|---|---|---|
| Hydrogel formulation (A) | 22400 | 5101 | 0.89 |

The fourth characteristic analyzed was the complex viscosity, including determining the elastic storage modulus (G') and the loss modulus (G"). Determination of in vitro elastic and storage rheological properties of the hydrogel gives key information regarding the formulation's behavior upon application of energy. This information predicts the performance of the hydrogel in different phases of its life cycle, e.g., during shelf storage, upon injection, and during submucosal space residence. This analysis gives key information regarding the viscosity changes and elastic behavior on temperature modulation.

The hydrogel formulations described herein can be a viscoelastic material and therefore exhibit both viscous and elastic behavior. Such viscoelastic materials can be considered a combination of both ideal types of materials: purely viscous fluids and ideally elastic solids. The flow properties of a purely viscous material can be determined in a simple flow experiment. If the material deforms at a constant rate the applied constant stress is constant and described by a simple relationship known as Newton's law. Such liquids are known as Newtonian fluids, and the material constant is referred to as Newtonian viscosity. For an elastic solid material (e.g., a steel spring or cross-linked rubber), a simple linear relationship exists between the stress and the strain. The material deforms instantaneously when subjected to a sudden stress and the strain will remain constant until the stress is removed. There is no loss of energy, and the solid will return to its original shape (the deformation is fully reversible). The material constant is the modulus of the material. The equation relating the stress and the strain is known as Hooke's law. In reality, most materials lie somewhere in-between these two extremes.

The elastic or storage modulus defines gives information about the amount of structure present in a material. It represents the energy stored in the elastic structure of the sample. If it is higher than the loss modulus, the material can be regarded as mainly elastic, i.e., the phase shift is below 45°. The loss modulus represents the viscous part or the amount of energy dissipated in the sample. The "sum" of loss and storage modulus is the so-called complex modulus G*. The complex viscosity η* is the standard parameter used in this case and can be calculated directly from the complex modulus. For the uses described herein (e.g., for mucosal lift), a hydrogel formulation with a high storage and loss modulus with a corresponding higher complex viscosity would be advantageous at body temperature. This would be clinically relevant through the indication that the formulation has significant viscoelastic properties and does not behave like a liquid, therefore allowing the formulation to reside in the submucosal space longer and provide a durable mucosal lift, reducing the risk of perforation of the deep muscle layer.

To analyze the complex flow viscosity, rheological analysis of the hydrogel formulation was performed both at 22±0.1° C. and 37±0.1° C. using an AR 2000 controlled stress/controlled rate rheometer (TA instruments, New Jersey, USA). Oscillatory analysis of each formulation under examination was performed after determination of its linear viscoelastic region at 22±0.1° C. and 37±0.1° C., where stress was directly proportional to strain and the storage modulus remained constant. Frequency sweep analysis was performed over the frequency range of 0.1-10.0 Hz following application of a constant stress and standard gap size was 0.1 mm for each sample. Storage modulus (G') and loss modulus (G"), the complex viscosity (η'), and the loss tangent (tan δ) were determined. In each case, the dynamic rheological properties of at least five replicates were examined. Complex viscosity is not the same as apparent viscosity and is a function of shear rate. Normal saline (Baxter, Deerfield, Ill.) and Eleview™ (Aries Pharmaceuticals, CA, USA) were used as reference agents.

Figure 6:
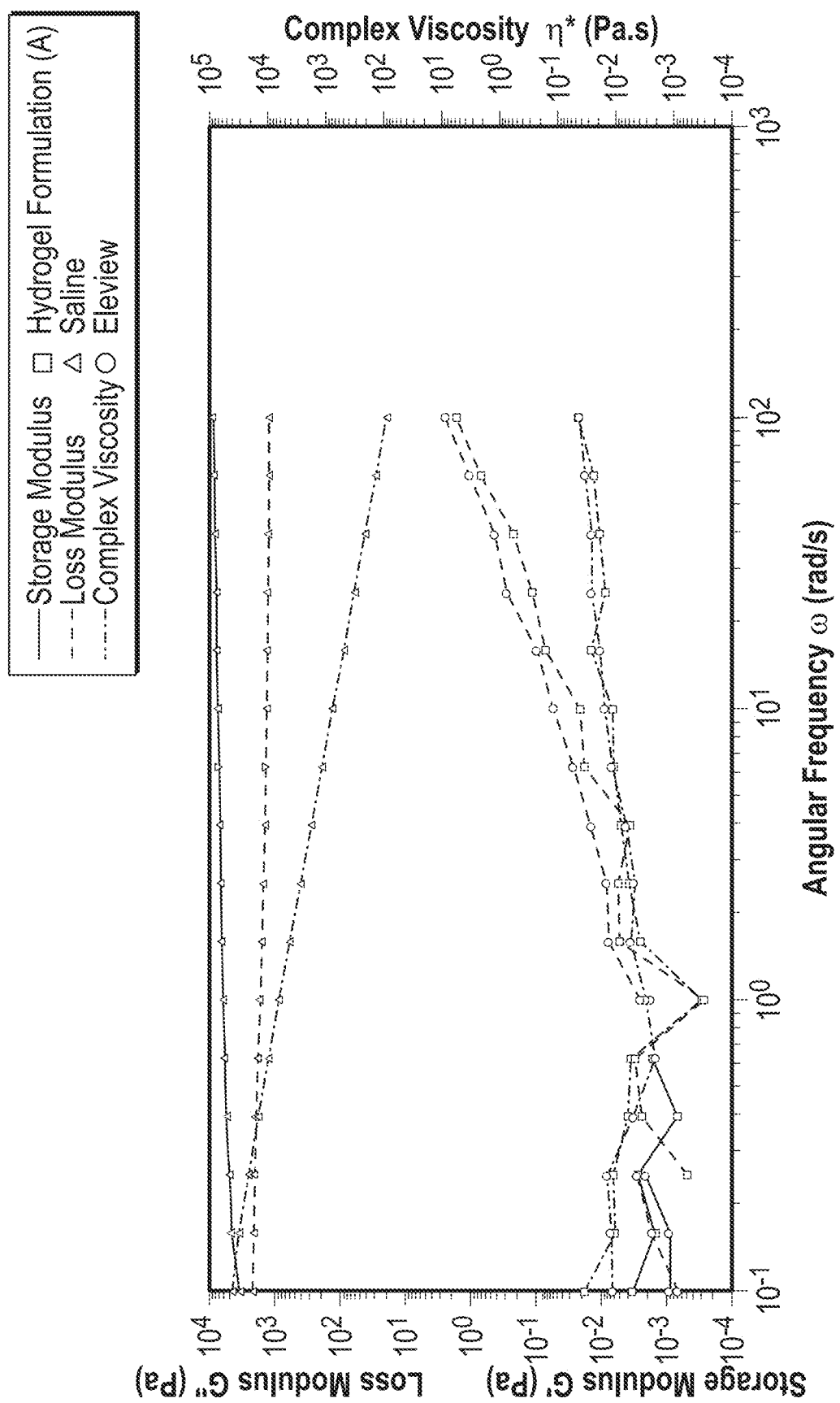
FIG. 6 shows results of viscoelastic property analysis for a hydrogel formulation relative to controls at 37° C.

The viscoelastic properties of the hydrogel formulation compared to reference agents are shown in Table 5 below and in FIG. 6. As can be seen, the hydrogel formulation shows significant viscoelastic (non-Newtonian) behavior under physiological conditions. In comparison, the reference agents showed no characteristics of viscoelasticity at physiological parameters, i.e., they remain liquid (Newtonian) at body temperature.

TABLE 5

Viscoelastic Properties

| Agent | G' (Storage Modulus Pa) | G" (Loss Modulus Pa) | Complex viscosity (mPa · s) | Tan (delta) |
|---|---|---|---|---|
| Normal Saline | −0.11 | 0.02 | 11 | −0.18 |
| Eleview ™ | −0.14 | 0.05 | 15 | −0.37 |
| Hydrogel formulation (A) | 7560 | 1347 | 768857 | 0.18 |

The fifth characteristic analyzed included the various mechanical properties of the hydrogel formulation. Determination of in vitro mechanical properties of the hydrogel formulations can give key information about the physical gel structure of the hydrogel, e.g., hardness, compressibility, cohesiveness, retraction force. Hardness refers to the resistance to localized plastic deformation induced by either mechanical indentation or abrasion. Hardness describes the formulations resistance to deformation when an external physical force is applied to it, mimicking the external electrosurgical device or even the endoscope placing force on it. Compressibility refers to the measure of the relative volume change of a fluid or solid as a response to a pressure (or mean stress) change. Cohesiveness refers to the action or property of the formulation molecules sticking together, being mutually attractive. It is an intrinsic property of the hydrogel that is caused by the shape and structure of its molecules, which makes the distribution of orbiting electrons irregular when molecules get close to one another. In other words, cohesion allows for surface tension. Maximum retraction force is the force required to overcome the surface tension of the hydrogel. Mechanical property information can be used to predict the hydrogel formulation behavior in different physiological and environmental conditions. A formulation with a high hardness, compressibility and retraction force with a low cohesiveness would be advantageous for use in submucosal lifting, as these properties can enable the formulation to retain its immediate post injection state and prevent leakage once incised e.g. when using electrosurgery.

Texture profile analysis (TPA) can be applied for mechanical characterization of semi-solid systems and gels. To determine these mechanical properties, the analytical probe of the TPA machine can be inserted into a semi-solid system to a defined depth, at a defined rate and extracted out at define rate. The resulting change in force can be plotted against time and provides the different mechanical properties such as hardness and compressibility. Texture profile analysis was performed using Software-controlled penetrometer (TA-XT Plus, Stable Micro System, UK) equipped with 5 kg load cell in texture profile analysis (TPA) mode. The formulations was transferred into a glass beaker (50 mL) at 37° C. An analytical probe was twice inserted into the formulation to a defined depth (15 mm) and at a defined rate (2 mm/s), allowing a delay period (15 s) between the end of the first and beginning of the second compression. Mechanical parameters (hardness, compressibility, cohesiveness and elasticity) were derived from the resultant force-time curve. Experiments were carried out at least three times. Normal Saline (Baxter, Deerfield, Ill.) and Eleview™ (Aries Pharmaceuticals, CA, USA) were used as reference agents.

The mechanical properties of the hydrogel formulations compared to reference agents are shown in Table 6 below. As shown, the hydrogel formulation (both A and B) exhibited significantly different mechanical properties than the reference agents, including increased hardness (e.g., 10-20 times higher hardness), compressibility (e.g., 20-30 higher compressibility), and retraction force (e.g., 5-10 times higher retraction force). The increased hardness indicates that the formulation will resist deformation while the higher compressibility indicates that the formulation will return to its original shape post application of an external force. The higher maximum retraction force denotes the increased force required to remove the agent upon residence in the submucosal space. Taken together, this data indicates that, upon injection into the submucosal space, the hydrogel formulation can provide a more durable, consistent mucosal lift than the reference agents.

TABLE 6

Mechanical Properties

| Agent | Hardness (N) | Compressibility | Cohesiveness | Max retraction force (N) |
|---|---|---|---|---|
| Normal Saline | 0.1 | 0.3 | 0.8 | −0.02 |
| Eleview ™ | 0.1 | 0.3 | 1 | −0.02 |
| Hydrogel formulation (A) | 1.9 | 7.1 | 0.02 | −1.5 |
| Hydrogel formulation (B) | 1.7 | 6.2 | 0.02 | −1.2 |

The sixth characteristic analyzed was the adhesion (e.g., adhesion to the mucosa and submucosa. Mucoadhesive force is defined as the force with which the hydrogel formulation binds to the mucosal surface at physiological temperature (37° C.). It is useful in assessing the formulation potential to interact with a mucosal surface and leakage behavior, e.g., after incision of the mucosal surface with electrosurgery. The mucoadhesive properties of the formulation can be determined by attaching mucous membrane (natural origin, e.g., porcine tissue, or artificial, e.g., mucin disks) to the bottom of the TPA analytical probe. In this situation, a formulation with a high mucoadhesive force would be advantageous, as a high mucoadhesive force will lead the formulation to reside in the submucosal space longer without leaking.

To show and compare the mucoadhesive strength of the disclosed formulation, porcine rectal mucosa was used. Mucosal tissue was obtained from newly sacrificed animals (<24 hours). Mucosa was separated from underlying tissues, washed, cut in smaller pieces and rinsed carefully. The samples were frozen at −20° C. until used. The mucoadhesive properties of formulations were evaluated with a 5 kg load cell using TA-XT Plus texture analyzer. A tissue section that possessed 2 mm thickness was taken from the inner part of the surface of the mucosal membrane (or mucin disc) and it was attached to the lower end of the probe (P 10 Perspex, θ: 10 mm) of the instrument with cyanoacrylate glue. The gels were packed into a 50 cc beaker and tests were conducted at 37° C. The probe holding the mucosa was lowered on to the surface of the gel with a constant speed of 0.1 mm·s−1 and a contact force of 0.2 N were applied. After keeping in contact for 120 s, the probe was then moved vertically upward at a constant speed of 0.1 mm·s$^{-1}$. Maximum force (the detachment force, F) was obtained from the force-distance graph. Tee area under the curve (AUC) was calculated from force-distance plot as the mucoadhesion (M). The equation given below was used to calculate the work of mucoadhesion (mJ/cm2). Each experiment was carried out five times and the results were evaluated statistically. Normal saline (Baxter, Deerfield, Ill.) and Eleview™ (Aries Pharmaceuticals, CA, USA) were used as reference agents.

Work of mucoadhesion=AUC/$r^2$ (mJ/cm$^2$)

where, $\pi r2$=the area of the mucosal surface being in contact with gel.

The mucoadhesion of the hydrogel formulation (A and B) compared to the reference agents is shown in Table 7 below. The formulation embodiments disclosed herein exhibited significantly higher mucoadhesion properties (e.g., 20-30 times higher mucoadhesion) compared to the reference agents. This property is advantageous, as the hydrogel formulations are therefore more likely to reside within the intestinal submucosal space and provide a more durable mucosal lift (e.g., upon incision with electrosurgical tools).

TABLE 7

Mucoadhesion

| Agent | Mucoadhesion (mJ/cm$^2$) |
|---|---|
| Normal Saline | 0.02 |
| Eleview ™ | 0.02 |
| Hydrogel formulation (A) | 5.3 |
| Hydrogel formulation (B) | 5.5 |

The seventh parameter analyzed was the electrical conductivity of the hydrogel. It is expected that electrosurgical may be applied in and around the hydrogel formulations injected site of administration, e.g., under and around an intestinal adenomatous polyp within the submucosal space. Hydrogel formulations can be characterized as either conductive or insulator in behavior. Purely conductive formulations permit conduction of electrical energy through the material. Purely insulator formulations permit no transmission of electrical energy. Transmission of electrical energy is relevant in these embodiments due to the use of electrosurgical energy in and around the lesion for removal e.g. an intestinal polyp. An ideal agent will be as much as an insulator as possible to prevent transmission of electrosurgical energy to the deeper intestinal wall causing immediate or delayed perforation. However, the formulation should also allow local transmission of electrosurgical energy to provide electrosurgical dissection via snare and endoscopic submucosal dissection devices (Olympus Snaremaster™, Dualknife™ or similar).

To analyze the conductivity, a magnetic stirring temperature controllable plate was used (TECA AHP-301MSP) allowing computer controlled accurate temperature modulation according to computer program selection. In this case, a temperature hold at 37° C. was used. Once the temperature of the agent was confirmed to be 37° C. for 5 minutes the probe of an Omega CDH-SD1 data logging conductivity meter was placed. Conductivity was measure in mS/cm. Normal saline (Baxter, Deerfield, Ill.) and Eleview™ (Aries Pharmaceuticals, CA, USA) were used as reference agents.

The conductivity of disclosed hydrogel formulations compared to reference agents is shown in Table 8 below. As shown, the hydrogel is a relative insulator (i.e., shows 50-75 times higher conductivity) compared to saline and Eleview™. Insulator characteristics can be favorable where electrosurgery energy is used as to prevent damage to the muscle layer of the intestine and immediate or delayed perforation.

TABLE 8

| Conductivity | |
|---|---|
| Agent | Conductivity (mS/cm) |
| Normal Saline | 15 |
| Eleview ™ | 6 |
| 3% sorbitol urological irrigation fluid | 0.1 |
| Hydrogel formulation (A) | 0.27 |
| Hydrogel formulation (B) | 0.26 |

The eighth characteristic analyzed was the change in performance of the hydrogel upon the addition of microbeads. Microbeads (coated or uncoated with additional materials, for example but not limited by coagulants, antibacterials or metallic coatings) can be added to the current hydrogel formulation embodiment to provide additional characteristics such as increased surface area for using less polymer, drug delivery e.g. antibiotics and anticoagulants and radiological visibility amongst others. In these experiments, polystyrene microbeads were used, however many different types are available and may be used. The hydrogel formulation may use the least amount of polymer as possible to facilitate the lowest possible viscosity for injection and provide increased surface area to allow polymeric networks to form (upon hydrogel formulation warming). Clinically, this can result in an injectable formulation that is easy to inject via a standard syringe, particularly along the long endoscopic needle injector catheters, at room temperature as well as a formulation that exhibits improved gelling upon warming. In addition, the cultivation of additional pharmaceutically derived properties may be useful in many clinical situations.

To analyze the effect of microbeads, microbeads were mixed into the hydrogel formulation according to % weight by volume. Rheological analysis was then undertaken as described previously to determine the viscosity.

Figure 7:
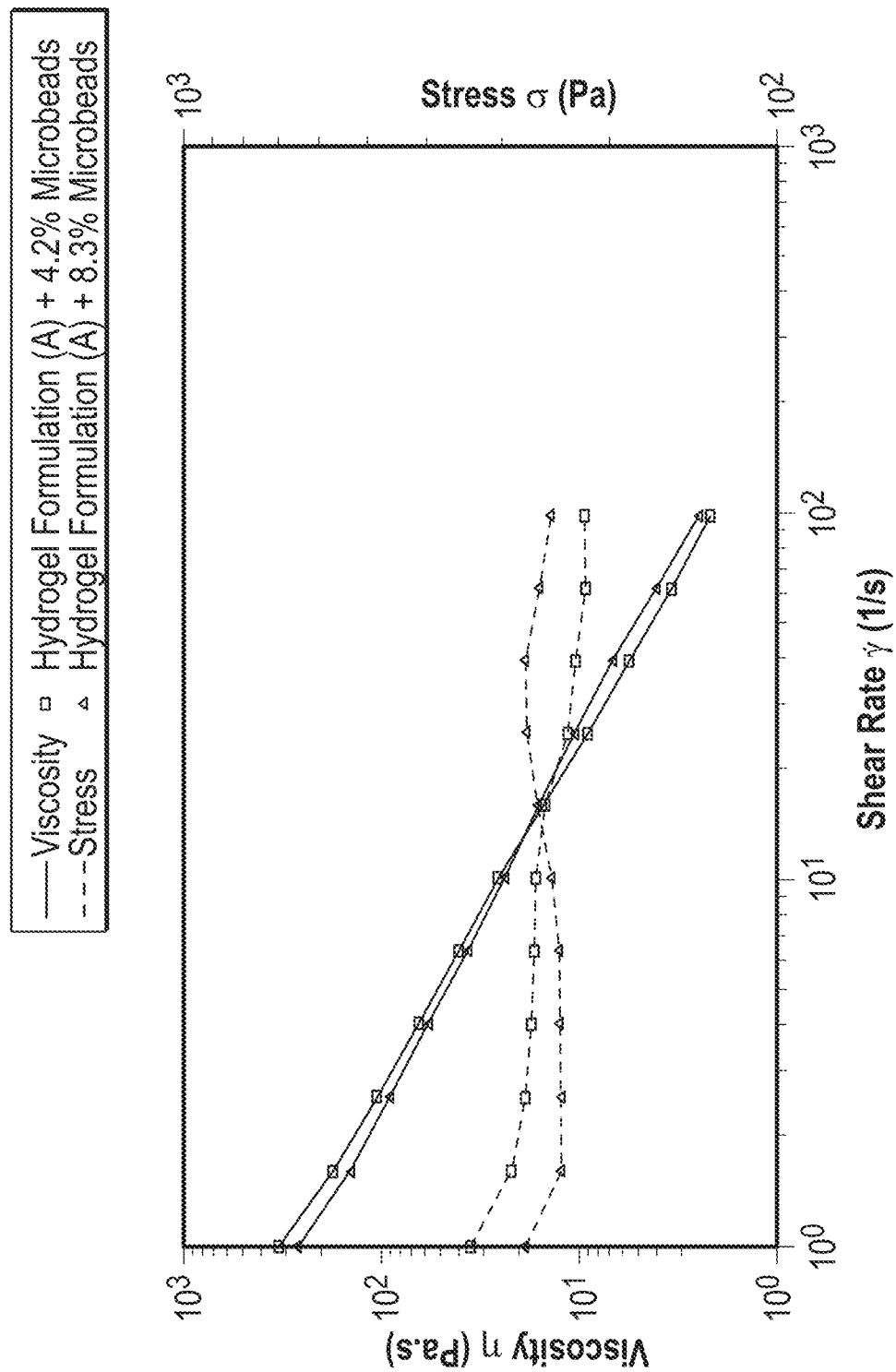
FIG. 7 shows results of flow sweep analysis for a hydrogel formulation with two different microbead percentages at 37° C.

Logarithmic flow sweep analysis of hydrogel formulations with addition of microbeads is shown below in Table 9 and in FIG. 7. As shown, the addition of microbeads increases the absolute viscosity.

TABLE 9

| Viscosity with Microbeads | |
|---|---|
| Agent | Viscosity (mPa · s) @ 37° C./Shear 10 s$^{-1}$ |
| Hydrogel formulation (A) + 4.2% microbeads | 25357 |
| Hydrogel formulation (A) + 8.3% microbeads | 23828 |
| Hydrogel formulation (A) | 22022 |

Figure 8:
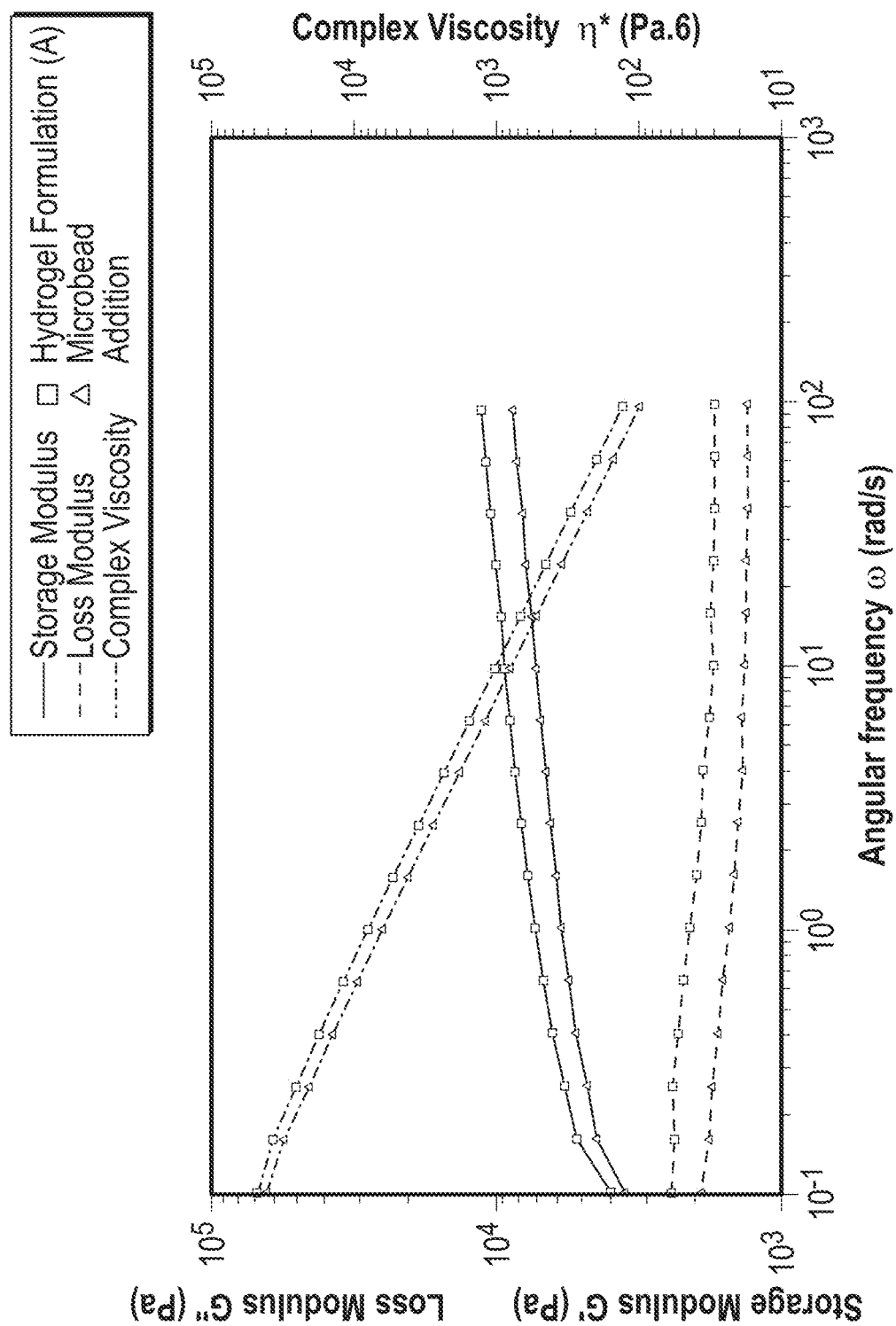
FIG. 8 shows results of viscoelastic property analysis for a hydrogel formulation with and without microbeads at 37° C.

Viscoelastic properties of microbeads added to hydrogel formulation embodiment tested via oscillatory rheometery at angular frequency of 10 rads per second and 37° C. are shown below in Table 10 and in FIG. 8. As shown, the addition of microbeads increases the viscoelastic performance of the hydrogel formulation.

TABLE 10

| Viscoelastic Properties with Microbeads | | | | |
|---|---|---|---|---|
| Agent | G' (Storage Modulus Pa) | G" (Loss Modulus Pa) | Complex viscosity (mPa · s) | Tan (delta) |
| Hydrogel formulation (A) + 4.2% microbeads | 8559 | 1596 | 870493 | 0.18 |
| Hydrogel formulation (A) + 8.3% microbeads | 6683 | 1248 | 679911 | 0.18 |
| Hydrogel formulation (A) | 7560 | 1347 | 768857 | 0.18 |

In some embodiments, the use of microbeads to modify viscoelastic characteristics can be employed within the hydrogels disclosed herein to augment the composition (e.g., to use less polymer material and provide the additional benefit of addition of pharmaceutically active components for example, but not to limited to, anticoagulation and antibacterial agents).

The ninth characteristic analyzed was the degree of mucosal lift post injection within the submucosal space in a porcine ex-vivo rectum. An important experimental result may be one where the intestinal mucosal lift is maintained at 90% of the original (immediately post-injection) height over 60 minutes using the hydrogel formulation. Clinically, this can result in a hydrogel formulation that provides a durable submucosal cushion, providing increased protection and safety. In addition, upon incision of the mucosa, the formulation can advantageously not leak out from the submucosal space to maintain the mucosal lift and safety.

To analyze the mucosal lift, a 5×5 cm section of fresh porcine rectum was placed on a temperature controlled heating pad set at 37° C. The tissue was allowed to equilibrate to 37° C. and temperature was verified with the use of an infrared thermometer (Etekcity Lasergrip™ 800). Upon the tissue reaching steady state of 37° C., 3 cc of the agent was injected into the submucosal space. Two parameters were measured over 1 hour: (1) dome height without incision—in millimeters; and (2) dome height with incision—in millimeters. Normal saline (Baxter, Deerfield, Ill.) and Eleview™ (Aries Pharmaceuticals, CA, USA) were used as reference agents.

Figure 9:
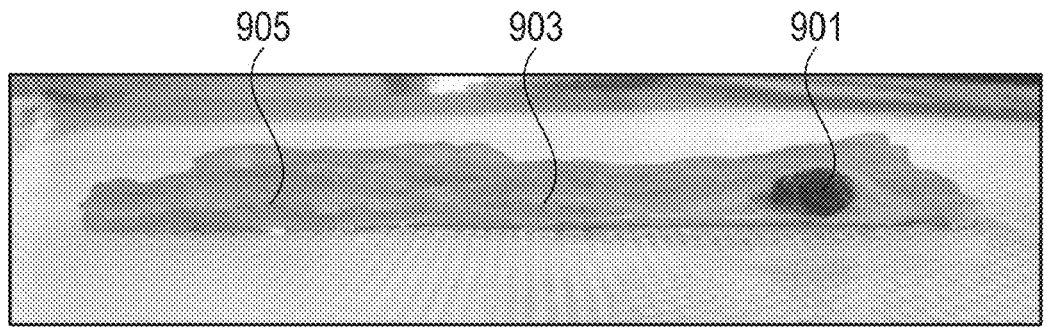
FIG. 9 shows use of a hydrogel relative to saline and Eleview™ over one hour after injection at 37° C.
Figure 10:
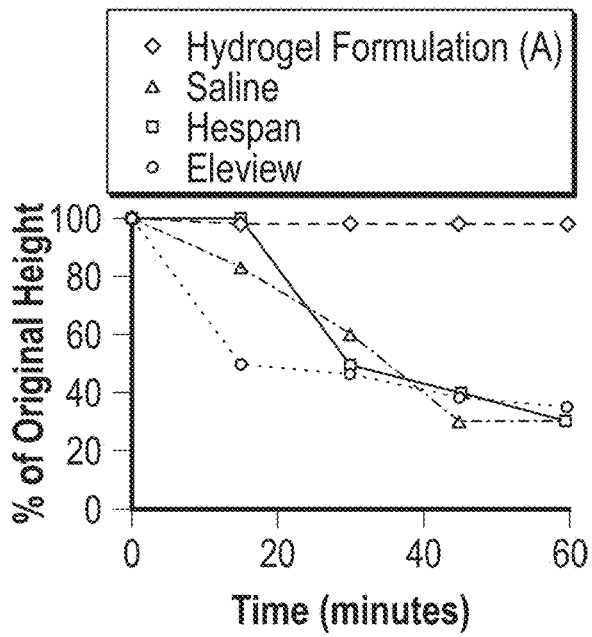
FIG. 10 shows height loss after injection for a hydrogel formulation relative to controls one hour after injection at 37° C.

Results are shown in FIGS. 9 and 10. As shown, the hydrogel formulation 901 exhibits a maintenance of the mucosal lift one hour post injection and therefore minimal dissipation within physiological parameters. In contrast, the saline 905, Eleview 903, and Hespan were only 50% present or less after 1 hour.

The tenth parameter examined was the ex-vivo mucosal surface area pigment marking after injection of the hydrogel formulation into the submucosal space of porcine rectum. The evaluation of the surface area that the pigment occupies provides a quantification of accuracy of the marking agent. An important experimental result would be one where the post injection surface area would be a close to the original injection area which would correspond to as precise and accurate over time. Clinically, this can result in a formulation that provides a deposition of pigment into the intestine submucosal space over time that allows for accurate detection.

Figure 11:
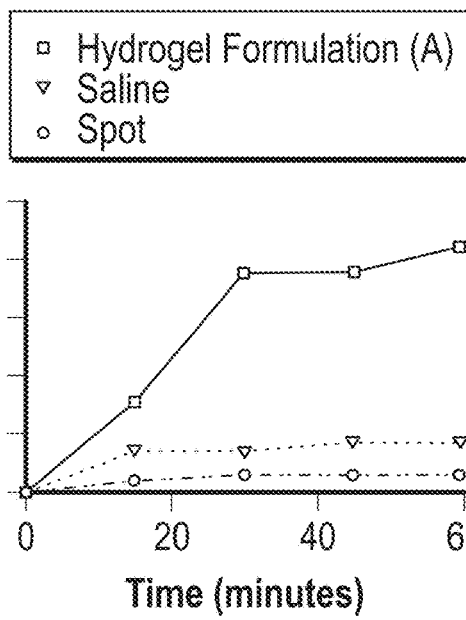
FIG. 11 shows surface area change for a hydrogel formulation relative to controls over one hour at 37° C.

To analyze the marking, a 5×5 cm section of fresh porcine rectum was placed on a grounding pad which itself was placed on a temperature controlled heating pad set at 37° C. Upon the tissue reaching steady state 37° C., 3 cc of agent was injected into the submucosal space using a standard 18G syringe. In this experiment Spot™ (GI Supply) was used as a reference agent, which is the current most widely used state of the art in marking agents. One parameter was measured over time—the surface area change over time without incision—in millimeters2/minute. The surface area change over one hour at 37° C. The hydrogel formulation exhibited the lowest surface area change followed by saline and spot (see FIG. 11). Advantageously, the hydrogel formulation exhibits minimal surface area change over one hour at physiological conditions compared to the reference agents, indicating minimal dissipation and providing a hydrogel formulation that is precise and accurate.

The eleventh parameter analyzed was the accuracy post injection into porcine rectum in-vivo over time. A key experimental result would be one where there was an accurate and consistent pigment deposition 60 days after injection. Clinically, this can result in a hydrogel formulation that will allow subsequent examinations of the patient where identification of the injected area is precise and accurate to the original injection site.

To test the accuracy, a chronic in-vivo study was performed to evaluate hydrogel's durability and accuracy post-injection to simulate that of a doctor injecting the formulation adjacent to pathology. The porcine model was used as the distal rectum and submucosa closely resembles that of human anatomy. The hydrogel formulation was delivered using a standard endoscope (Olympus GIF-190L) and endoscopic needle injector (Boston Scientific Interject 25G). The hydrogel formulations was injected into the distal rectum of pigs using standard endoscopic equipment. The pigs were kept alive post-procedure for 60 days and then sacrificed. The distal colon was removed and pigment area corresponding to the injection site was measured. Saline and Spot were used as reference agents.

Figure 12:
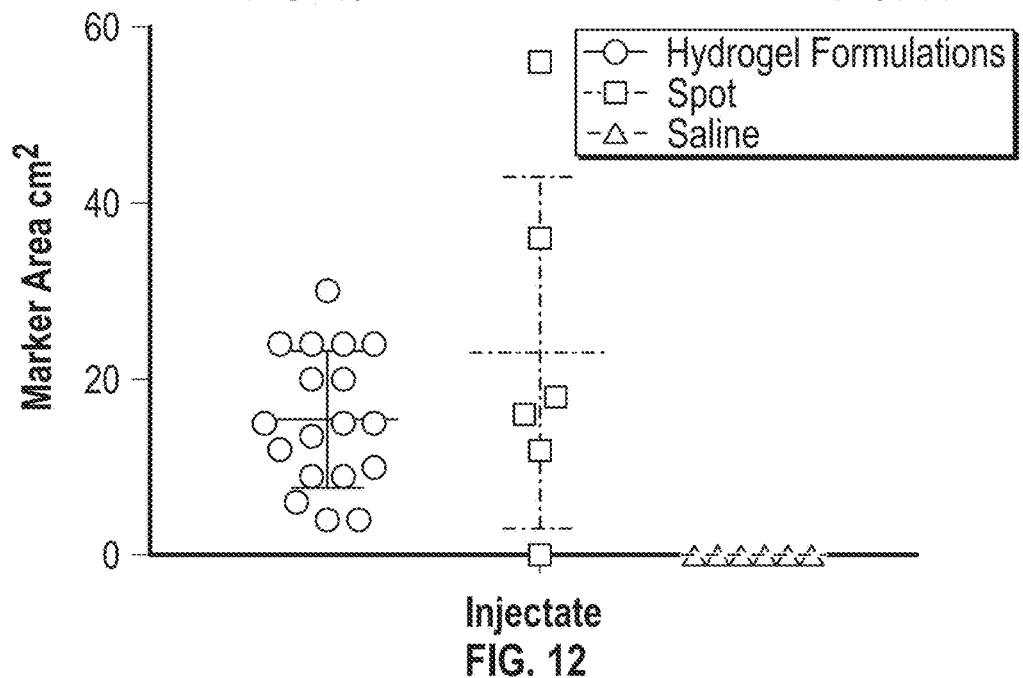
FIG. 12 shows the pigmented area of hydrogel formulations relative to controls.

The pigmented area of the disclosed hydrogel formulations described herein (circles) versus Spot (squares) and Saline (triangles), 60 days post-injection are shown in FIG. 12. As shown, the hydrogel formulation is more accurate and precise 60 days post injection compared to the reference agents. Saline disappeared completely during follow-up. This indicates that the disclosed formulation's dissipation profile allows for accurate and precise deposition of pigment into the intestine.

The twelfth parameter analyzed was the electrical conduction of the hydrogel formulation upon the application of electrosurgical energy. The quantification of electrosurgical conduction produced per unit time during electrosurgical tool contact was undertaken. This can be important clinically, as electrosurgical tool use will be a standard clinical event whilst using such formulations. Here, the conductivity in tissue was measured to indicate clinical relevance. An important experimental result would be one where there is no excessive electrosurgical contact between the submucosal area and the deeper muscle layer with the electrosurgical tool. Preventing unnecessary transmission of electrosurgical energy to the deeper intestinal wall can avert immediate or delayed perforation. Clinically, this can result in a hydrogel formulation that increases safety.

To analyze the electrical conduction, an ex-vivo tissue analysis using 5×5 cm section of fresh porcine rectum placed on a grounding pad, which itself was placed on a temperature controlled heating pad set at 37° C. The tissue was allowed to equilibrate to 37° C. and temperature was verified with the use of an infrared thermometer (Etekcity Lasergrip 800). Using a standard endoscopic electrosurgical generator (Olympus ESG-100) connected to an Olympus Snaremaster electrocautery snare, electrical energy was applied to the formulation(s). One parameter was measured: the degree of electrical energy transference from the submucosal space to the deeper intestinal wall. Saline was used as a reference agent.

Transference of electrical energy was confined to the submucosa for the hydrogel formulation compared to normal saline (where transference of electrical energy transfers through the muscle layer). Advantageously, using the hydrogel formulations disclosed herein, the electrical energy from the electrosurgical tool was focused within the submucosal space providing a safer submucosal agent to use compared to saline where the electrical energy transference to deeper muscle wall was pronounced.

Experimental Study 2

In a second experimental study, a plurality of hydrogel formulation as described were produced with varying amounts of carbomer or different types of pigment, and the effects on dome height and coloring in vivo were examined. The hydrogel formulation included Carbomer 1.9-2.5%, Poloxamer 1%, Xanthan Gum 1%, Sterile water 75% solution, buffer 25% solution and pigment. Pigments included in the study were Methylene Blue 1% solution and FDandC #1 1% solution. The method of producing the hydrogel formulation included mixing of the polymers and liquid for a minimum of 1 hour at 100 rpm stirring speed. After mixing, the solution was filtered and was then ready to use.

The objective of this study was to determine the performance of a submucosal injection formulation of a plurality of hydrogels of varying composition. The performance of the hydrogel formulations was compared to that of a control (Eleview™). The study included a determination of mucosal dome height post injection as well as an evaluation of device set-up time.

The total time for the hydrogel formulations (on average) to set up for injection relative to the time for Eleview™ is shown in Table 11 below. Set-up time was classified as the time taken to remove the agent from its packaging and prime a standard commercially available endoscopic injection needle device of 240 cm and 25 gauge in diameter. As indicated, the hydrogel formulation set up faster than the control (e.g., 3-5 times faster).

TABLE 11

Time to set up for injection

| Agent | Time (seconds) |
|---|---|
| Hydrogel formulation | 24.5 |
| Eleview ™ | 96 |

Figures 13A, 13B, 13C:
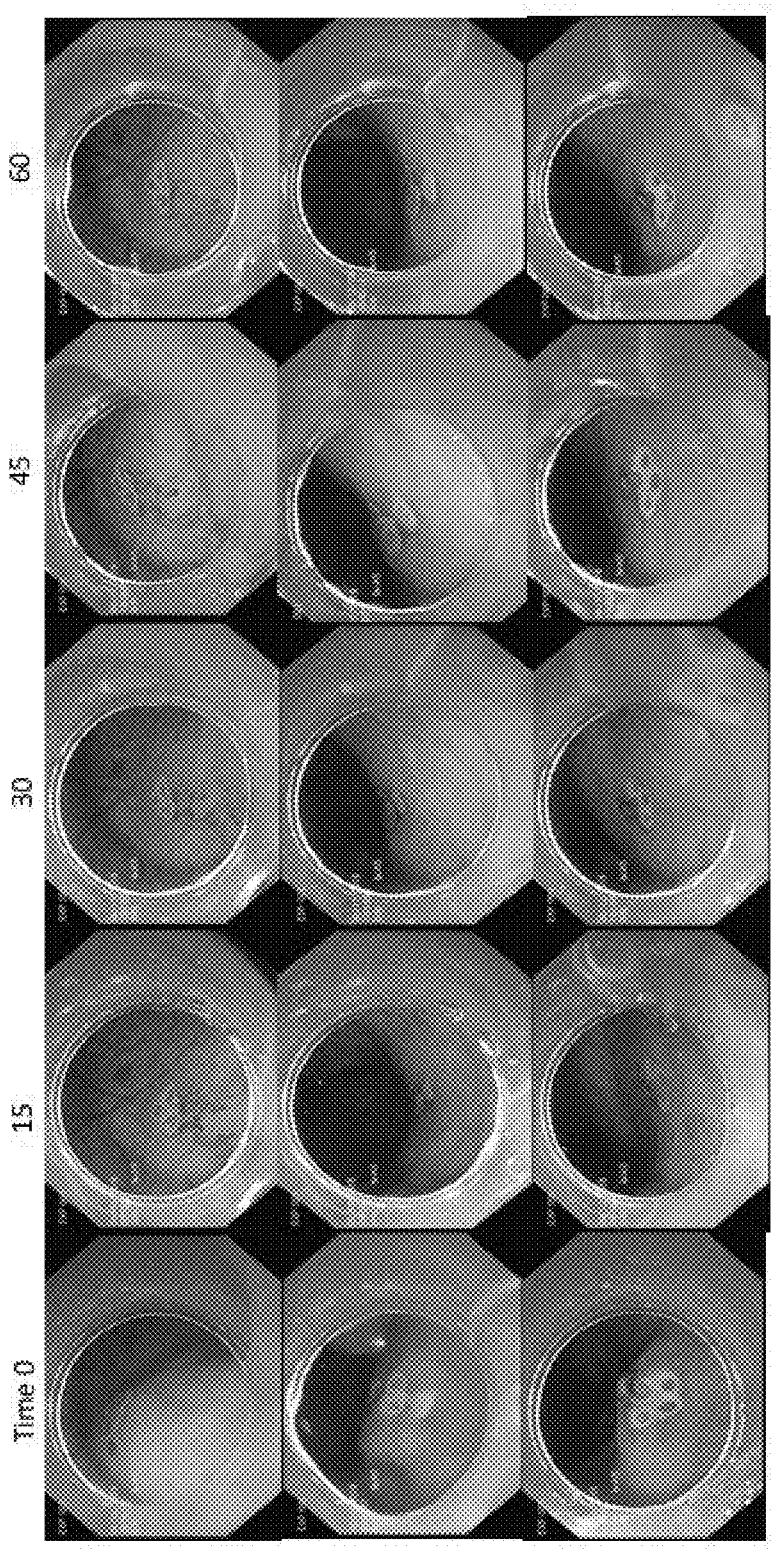

Additionally, FIGS. 13A-13O show photographs of the lift associated with the various hydrogel formulations relative to the control over time (at 0 minutes, 15 minutes, 30 minutes, 45 minutes, and 60 minutes). FIGS. 13A-13C show the elevation achieved through the use of the hydrogel formulation (FIG. 13A) relative to the Eleview™ control (FIGS. 13B and 13C) over time. As shown, the Eleview™ resulted in no elevation at 60 minutes, in contrast to the hydrogel formulation, which still showed significant lift. FIGS. 13D-F show the elevation achieved with a hydrogel of varying carbomer concentration relative to the control. As shown, the hydrogel formulation with 2% carbomer (FIG. 13E) produced the most pronounced dome, followed by the hydrogel formulation with 1.6% carbomer (FIG. 13D). The Eleview™ control (FIG. 13F) again showed little lift at 60 minutes. FIG. 13G-13I also show the elevation achieved with a hydrogel of varying carbomer concentration relative to the control. As shown, the hydrogel formulation with 2% carbomer (FIG. 13G) produced the most pronounced dome, followed by the hydrogel formulation with 1.9% carbomer (FIG. 13I). The Eleview™ control (FIG. 13H) again showed little lift at 60 minutes. FIGS. 13J-K all show that a hydrogel formulation with 2.5% carbomer results in substantial lift through 60 minutes. Finally, FIGS. 13M-13O show how different dyes can affect the lift and/or coloring upon injection. The hydrogel formulation with methylene blue (FIG. 13M) and the hydrogel formulation with FDandC #1 (FIG. 13N) both resulted in lasting color and lift at 60 minutes while the Eleview™ control (FIG. 13O) did not.

The experimental results indicated that concentrations of carbomer about 1.9%-2.5%, such as 2.0%, with or without dye produce the best lift through 60 minutes (e.g., through the average time of a submucosal lift procedure). Additionally, concentrations of 2.5% or below can advantageously ensure that the hydrogel formulation dissipates within 90 minutes or so, thereby enhancing safety of the formulation. Further, controlled incision of the intestinal mucosa as seen in this experiment demonstrates appropriate electrosurgical conduction, which can be advantageous in removal of pathological lesions e.g. colon polyps.

Experimental Study 3

In a third experimental study, the rheological properties of a hydrogel comprising, the hydrogel includes poloxamer (5%), carbomer (1.9-2.5%), xanthum gum (1%), sterile water (74%), pigment (1%) and a buffer (25%) were compared to a constant (Eleview™) In particular, the difference in viscosities at 1 rad/s of force (simulating stationary) relative to 10 rad/s of force (simulating injection force) was analyzed. In order to make injection of the formulation easy while still maintaining substantial viscosity upon injection, it is advantageous for the viscosity of the hydrogel formulation to be significantly lower upon the application of force than the viscosity of the hydrogel formulation when stationary. The results are shown in Table 12 below. As indicated, the hydrogel formulation at 22° C. and at 10 rad/s can have a viscosity that is less than 50%, such as less than 30% of the viscosity at 22° C. and at 1 rad/sec. Moreover, the hydrogel formulation at 37° C. and at 10 rad/s can have a viscosity that is less than 30%, such as less than 20% of the viscosity at 37° C. and at 1 rad/sec. As shown, the difference between the viscosities of the hydrogel formulation when stationary and during injection is much higher than the difference between the viscosities of the control (Eleview™) when stationary versus injected. Further, as shown below, the viscosity of the hydrogel formulation at 37° C. can be less than 10 Pa·s, such as less than 5 Pa·s, such as less than 4 Pa·s at shear rates of up to 10 rad/s. Further, the viscosity of the hydrogel at 37° C. can be greater than 0.2 Pa·s, such as greater than 0.3 Pa·s, such as greater than 0.5 Pa·s. These viscosities can advantageously ensure that the hydrogel spreads evenly and dissipates timely while still providing adequate lifting during the submucosal lift procedure.

TABLE 12

Rheological Properties

| | Viscosity (Pa · s) | | | |
|---|---|---|---|---|
| | 22° C. | | 37° C. | |
| Agent | 1 rad/s | 10 rad/s | 1 rad/s | 10 rad/s |
| Hydrogel formulation | 0.7983 | 0.3131 | 3.1367 | 0.5917 |
| Eleview ™ | 0.0051 | 0.0048 | 0.0100 | 0.0036 |

Experimental Study 4

In a fourth experimental study, the effects of electron beam sterilization on the hydrogel formulation were examined. The formulation consisted of poloxamer (5%), carbomer (2.5%), xanthan gum (1%), water by solution (50%), buffer (25%) and 1% methylene blue (25%). That is, electron beam sterilization can be used to ensure sterility before use of the hydrogel formulation for use in the body. Such sterilization, however, can raise the temperature of the hydrogel and result in altering the characteristics of the hydrogel. In particular, the percentage height maintenance of the hydrogel over time can be decreased as a result of electron beam sterilization. It was determined that a total dosage of 20-30 kGy of electron beam radiation (with 1-3 refrigeration cycles therebetween to decrease the temperature of the gel) can advantageously result in gels with a low dissipation rate at 45-60 minutes.

CONCLUSIONS

As used herein, the term "viscosity" refers to the resistance of a liquid or semisolid against flow. The flow of liquids or semisolids is described by viscosity, or, more precisely, by shear viscosity η. The shear viscosity of a fluid expresses its resistance to shearing flows, where adjacent layers move parallel to each other with different speeds. Common units of measurement of viscosity are the pascal-second (Pa·s), the poise (P) and "cP" centipoises. 1 poise (P) corresponds to 0.1 pascal-second (Pa·s); 1 centipoise (cP) corresponds to 1 millipascal-second (mPa·s).

As used herein, the term "non-toxic" refers to compounds that are not harmful to the area coming in contact with the compound. In some instances, the term may refer to compounds that are not harmful or toxic to the body in general. In other instances, the term refers to the compound being safe for use and not harmful in the concentration and quantity being used at any one time.

As used herein, the term "bio-compatible" refers to compounds that are not harmful to tissue with which they come into contact with. In some instances, the term refers to compounds or agents that do not elicit an immune response from the tissue or systems that it comes into contact with. In other instances, the term refers also to the compound's metabolized products being not harmful to the tissue and systems it comes into contact with.

As used herein an "aqueous fluid" (e.g., a solution, suspension, etc.) is one which contains water, typically from 70 wt % to 99 wt % or more water. In addition, a co-solvent may be added e.g., normal saline typically from 10 wt % to 90 wt %.

As used herein a hydrogel is a material (in anhydrous or hydrated form) that contains polymers that form complex networks upon reaction to external stimuli e.g. temperature and pH.

As used here, a "polymer" is a material that contains bonded repeated subunits that are the same, also termed monomers. The number of monomers that make up the polymer varies according to the specifications, but in the hydrogel formulations described herein can refer to up to 10,000 subunits. In the anhydrous form, the polymers can make up to 99% of the total weight of the hydrogel. Monomers may also be free monomers that make up the constituents of the polymer. In the hydrated form polymers may make up 0.001% to 50% of the volume. If a polymer contains single repeated monomer, it is known as a homopolymer. If a polymer has 2 repeated monomers it is known as a co-polymer. A block co-polymer refers to that co-polymer that contains 2 or more polymer chains of different components. Triblock contains 3 polymer chains and so on. The constituents of a block copolymer can be both made up of homopolymers and co-polymers.

In some embodiments, the hydrogels described herein do not include poly(propylene oxide). In some embodiments, the hydrogels do not include poly(ethylene oxide). In some embodiments, the hydrogel composition does not include an oily component.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. An injectable medical composition comprising:
   an acrylate comprising a poly(acrylic acid) copolymer and a solvent,
   wherein the composition has a first viscosity at temperatures below a body temperature from 35.5° C.-38.5° C. and a second viscosity that is greater than 2500 mPa·s when exposed to the body temperature, the first viscosity lower than the second viscosity,
   wherein the composition, 15 minutes after exposure to the body temperature, has a third viscosity that is at least 50% of the second viscosity, and
   wherein the composition, at 90 minutes after exposure to the body temperature, has a fourth viscosity that is less than the second viscosity and the third viscosity.

2. The composition of claim 1, wherein the fourth viscosity is less than 100 mPa·s.

3. The composition of claim 1, wherein the second viscosity is from 2500 mPa·s to 20000 mPa·s at the body temperature.

4. The composition of claim 1, wherein a hardness of the composition at the body temperature is between 1N and 10N.

5. The composition of claim 1, wherein a compressibility of the composition at the body temperature is less than 10N.

6. The composition of claim 1, wherein the poly(acrylic acid) copolymer in the composition is between 0.2% and 5% w/v.

7. The composition of claim 1, wherein the poly(acrylic acid) copolymer comprises allyl sucrose or allyl pentaerythritol.

8. The composition of claim 1, wherein the composition further comprises poly(ethylene oxide)-b-poly(propylene oxide)-b-poly(ethylene oxide).

9. The composition of claim 1, wherein the solvent comprises sodium acetate.

* * * * *